US008431615B2

(12) United States Patent
Chu et al.

(10) Patent No.: US 8,431,615 B2
(45) Date of Patent: Apr. 30, 2013

(54) DOSE FORMS

(75) Inventors: Hui-May Chu, Natick, MA (US); Ene Ette, Framingham, MA (US); Lindsay McNair, Allston, MA (US); John Alam, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 942 days.

(21) Appl. No.: 11/264,746

(22) Filed: Oct. 31, 2005

(65) Prior Publication Data

US 2006/0105978 A1    May 18, 2006

Related U.S. Application Data

(60) Provisional application No. 60/722,746, filed on Sep. 30, 2005, provisional application No. 60/682,091, filed on May 17, 2005, provisional application No. 60/679,402, filed on May 9, 2005, provisional application No. 60/623,542, filed on Oct. 29, 2004.

(51) Int. Cl.
*A61K 38/21* (2006.01)
*A61K 38/00* (2006.01)
*A61K 31/14* (2006.01)

(52) U.S. Cl.
USPC ........... 514/588; 514/4.3; 514/894; 424/85.7; 424/85.4

(58) Field of Classification Search ........................ None
See application file for complete search history.

(56) References Cited

U.S. PATENT DOCUMENTS

2003/0050277 A1*  3/2003  Kajimoto et al. ................ 514/54
2003/0186895 A1* 10/2003  Llinas-Brunet et al. ........ 514/18

FOREIGN PATENT DOCUMENTS

| WO | WO 0218369 A2 | * | 3/2002 |
| WO | WO 02/18369 | * | 7/2002 |
| WO | WO 2005/123076 A2 | | 12/2005 |

OTHER PUBLICATIONS

Fried et al. (2002), N. Eng J. Med, vol. 347, No. 13, pp. 975-982.*
Anonymous, "Vertex Pharmaceuticals Press Release," Sep. 7, 2004, Retrieved from the Internet: URL: http://www.vpharm.com/Pressrelease2004/pr090704.html.
Tan, Seng-Lai, "Strategies for Hepatitis C Therapeutic Invention: Now and Next," Current Opinion in Pharmacology, Elsevier Science Publishers, NL, vol. 4, No. 5, Oct. 2004, pp. 465-470.
Anonymous, "Preclinical Data Suggest Potential for Oral Combination Approaches for HCV," May 31, 2004, Retrieved from the Internet: URL: www.newsrx.com/print.php?articleID=171197.
Perni, Robert B., et al., "972 VX-950: The Discovery of an Inhibitor of the Hepatitis C NS3.4A Protease and a Potential Hepatitis C Virus Therapeutic," Hepatology, Williams and Wilkins, Baltimore, MD, vol. 38, 2003, p. 624A.
Reesink, Henk W., et al, "Initial Results of a Phase 1B, Multiple-Dose Study of VX-950, a Hepatitis C Virus Protease Inhibitor," Gastroenterology, vol. 128, No. 4, Supplement 2, Apr. 2005, p. A697, A696 & Annual Meeting of the American Gastroenterological Association Digestive Disease Week, Chicago, IL,May 14-19, 2005, ISSN: 0016-5085.
Reesink, Henk W., et al, "Final Results of a Phase 1B, Multiple-Dose Study of VX-950, a Hepatitis C Virus Protease Inhibitor," Hepatology, vol. 42, No. 4, Supplement 1, Oct. 2005, pp. 234A-235A & 56th Annual Meeting of The American Association for the Study of Liver Diseases, San Francisco, CA. Nov. 11-15, 2005, ISSN: 0270-9139.
Lin, C., et al., In vitro resistance studies of hepatitis C virus serine protease inhibitors, VX-950 and BILN 2061: structural analysis indicates different resistance mechanisms, J Biol Chem. Apr. 23, 2004;279(17):17508-14. Epub Feb. 6, 2004.
Lin, K., et al., Combination of a Hepatitis C Virus NS3•4A Protease Inhibitor with IFN-α Synergistically Inhibits Viral RNA Replication and Facilitates Viral RNA Clearance in Replicon Cells, Antimicrob. Agents Chemo. 2004;48:4784-4792.
Perni, R.B., et al., Preclinical profile of VX-950, a potent, selective, and orally bioavailable inhibitor of hepatitis C virus NS3-4A serine protease, Antimicrob Agents Chemother. Mar. 2006;50(3):899-909.
Lin, C., et al., Discovery and development of VX-950, a novel, covalent, and reversible inhibitor of hepatitis C virus NS3.4A serine protease, Infect Disord Drug Targets. Mar. 2006;6(1):3-16. Review.
Lin, K., et al., VX-950, a novel hepatitis C virus (HCV) NS3-4A protease inhibitor, exhibits potent antiviral activities in HCV replicon cells, Antimicrob Agents Chemother. May 2006;50(5):1813-22.
Thomson, J.A., et al., Hepatitis C virus NS3-4A protease inhibitors: countering viral subversion in vitro and showing promise in the clinic, Curr Opin Drug Discov Devel. Sep. 2006;9(5):606-17. Review.
Reesink, H.W., et al., Rapid decline of viral RNA in hepatitis C patients treated with VX-950: a phase lb, placebo-controlled randomized study, Gastroenterology. Oct. 2006;131(4):997-1002.
Kwong, A.D., et al., Beyond interferon and ribavirin: Antiviral therapies for hepatitis C virus, Drug Discovery Today: Therapeutic Strategies. 2006;3:211-220.
Perni, R.B., et al., VX-950: The Discovery of an Inhibitor of the Hepatitis C NS3•4A Protease and Potential Hepatitis C Virus Therapeutic, *Hepatology 2003*;38:624A.
Lin, K., et al., VX-950: a tight-binding HCV protease inhibitor with a superior sustained inhibitory response in HCV replicon cells, *Hepatology* 2003;38:222A.
Kwong, A.D., VX-950: An Orally Bioavailable Inhibitor of the HCV ns3-4A Protease; a potential HCV therapeutic, 5th Antiviral Drug Discovery and Development Summit, Cherry Hill, NJ, Mar. 29-30, 2004.
Reesink, H.W., et al., Initial results of a Phase 1b, multiple dose study of VX-950, a hepatitis C virus protease inhibitor, Gastroenterology, vol. 128, Issue 4, Supplement 2, Apr. 2007, pp. A-697.
Kieffer, T.L., et al., Genetic Heterogeneity in the HCV NS3 Protease of Untreated Genotype 1 Patients Has Little Effect on the Sensitivity to VX-950, 12th International Conference on Hepatitis C Virus and Related Viruses, Montreal, Canada, Oct. 2-6, 2005.

(Continued)

*Primary Examiner* — Christine J Saoud
*Assistant Examiner* — Jegatheesan Seharaseyon
(74) *Attorney, Agent, or Firm* — Ronigman Miller Schwartz and Cohn LLP; Noel E. Day; Jonathan P. O'Brien

(57) ABSTRACT

The present invention relates to antiviral therapies and compositions for treating or preventing Hepatitis C infections in patients and relates to other methods disclosed herein. The invention also relates to kits and pharmaceutical packs comprising compositions and dosage forms. The invention also relates to processes for preparing these compositions, dosages, kits, and packs.

2 Claims, 13 Drawing Sheets

OTHER PUBLICATIONS

Kieffer, T.L., et al., Genetic heterogeneity in the HCV NS3 protease of untreated genotype 1 patients has little effect on the sensitivity to Vx-950, *Hepatology 2005*;42:537A.

Kwong, A.D., VX-950: A Novel HCV Protease Inhibitor, HepDART 2005, Big Island, Hawaii, Dec. 12-15, 2005.

Kwong, A.D., HCV Protease Inhibitors: Activity and Resistance, 13$^{th}$ Conference on Retroviruses and Opportunistic Infections (CROI), Denver, CO, Feb. 5-8, 2006.

T. Kieffer, et al., Wild-type HCV NS3 protease re-emerges during follow-up after 14 days of dosing with VX-950 in patients with genotype 1 HCV, *Journal of Hepatology*, vol. 44, Supplement 2, Apr. 2006, p. S7.

R. Ramachandran, et al., Anti-viral activity of VX-950 resolves expression of an HCV-associated gene signature, *Journal of Hepatology*, vol. 44, Supplement 2, Apr. 2006, p. S223.

H.W. Reesink, et al., Initial results of a 14-day study of the hepatitis C virus inhibitor protease VX-950, in combination with peginterferon-alpha-2a, *Journal of Hepatology*, vol. 44, Supplement 2, Apr. 2006, p. S272.

E.J. Lawitz, et al., 28 Days of the Hepatitis C Protease Inhibitor VX-950, in Combination With PEG-Interferon-ALFA-2a and Ribavirin, is Well-Tolerated and Demonstrates Robust Antiviral Effects, *Gastroenterology*, vol. 131, Issue 3, Sep. 2006, pp. 950-951.

Lawitz, E., et al., 28 days of the hepatitis C protease inhibitor telaprevir (VX-950), in combination with peginterferon-alfa-2a and ribavirin, is well-tolerated and demonstrates robust antiviral effects, 12$^{th}$ International Symposium on Viral Hepatitis and Liver Disease (ISVHLD), Paris, France, Jul. 1-5, 2006.

Kieffer, T., et al., Combination of Telaprevir (VX-950) and Peg-IFN-alfa Suppresses Both Wild-type Virus and Resistance Variants in HCV Genotype 1-Infected Patients in a 14-day Phase 1b study, *Hepatology 44* (2006) (suppl 2), p. 222A.

M. Rodriguez-Torres, Current status of subjects receiving peginterferon alfa-2a (PEG-IFN) and ribavirin (RBV) follow-on therapy after 28-day treatment with the hepatitis C protease inhibitor telaprevir (VX-950), PEG-IFN and RBV, *Hepatology 44* (2006) (suppl 2), p. 532A.

Forestier, N., et al., Current status of subjects receiving peg-interferon-alfa-2a (PEG-IFN) and ribavirin (RBV) after a 14-day study of the hepatitis C protease inhibitor telaprevir (VX-950), with PEG-IFN, *Hepatology 44* (2006) (suppl 2), p. 614A.

Alger, Lynsey, Advances in Antiviral Therapeutics—SMi's Second Annual Conference, IDrugs 2005, Dec. 1-2, 2004, pp. 29-33, vol. 8 No. 1, London, UK.

Antiinfective Therapy, Drug Data Report 2002, 24(6), pp. 534-541.

Lin, Kai, et al., In Vitro Combination Studies of VX-950 (a HDV Protease Inhibitor) or VX-497 (an IMPDH Inhibitor), Two Novel Anti-HCV Clinical Candidates, with IFN-a, Antiviral Research 62 (2004), May 2-6, 2004, pp. A1 and A52, Tucson, AZ, USA.

Lin, Kai, et al., In Vitro Combination Studies of two Novel HCV Clinical Candidates, VX-950 (a HCV Protease Inhibitor) or Merimepodib (MMPD, VX-497, an IMPDH Inhibitor), with Interferon Alpha, International Conference on Antiviral Research, May 2-6, 2004, Tucson, AZ, USA.

Chu, Hui-May, et al., Results of a Phase I Single-Dose Escalation Study of the Hepatitis C Protease Inhibitor VX-950 in Healthy Volunteers, AASLD Abstracts, 2004, p. 735A, vol. 40, No. 4, Suppl. 1, Hepatology.

Chu, Hui-May, et al., Results of a Phase I Single-Dose Escalation Study of the Hepatitis C Protease Inhibitor VX-950 in Healthy Volunteers, 55th Annual Meeting of the American Association for the Study of Liver Diseases, Oct. 29-Nov. 2, 2004, Boston, MA.

\* cited by examiner

Mean Concentration Time Profiles by Dose Levels

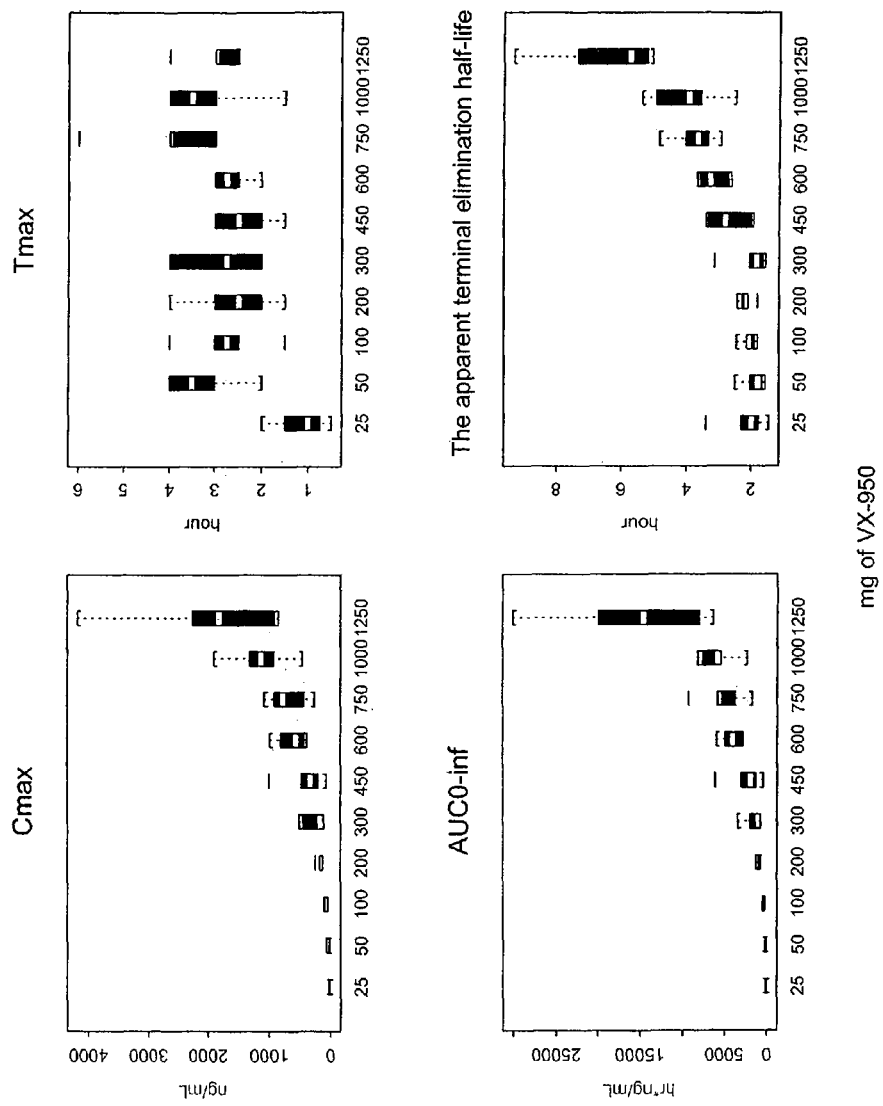
PK Parameters for Single Dose Escalation (Part A)
FIGS. 2A-D

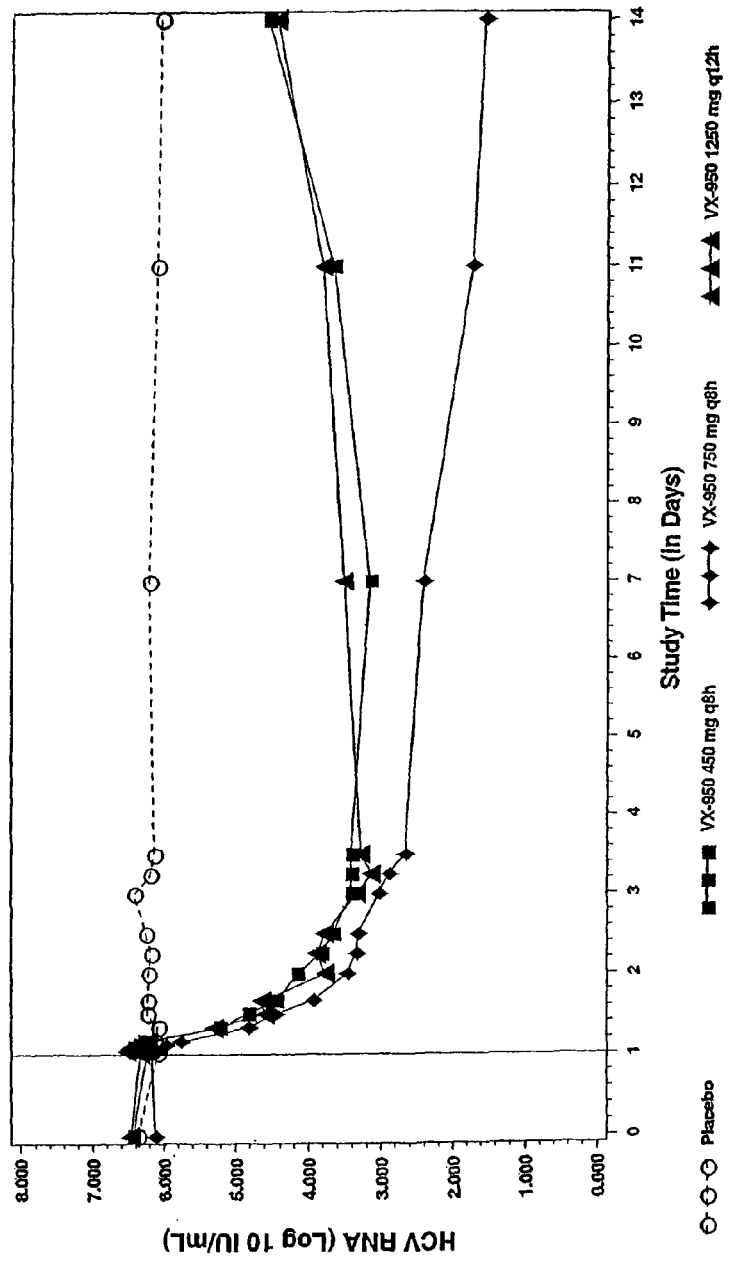

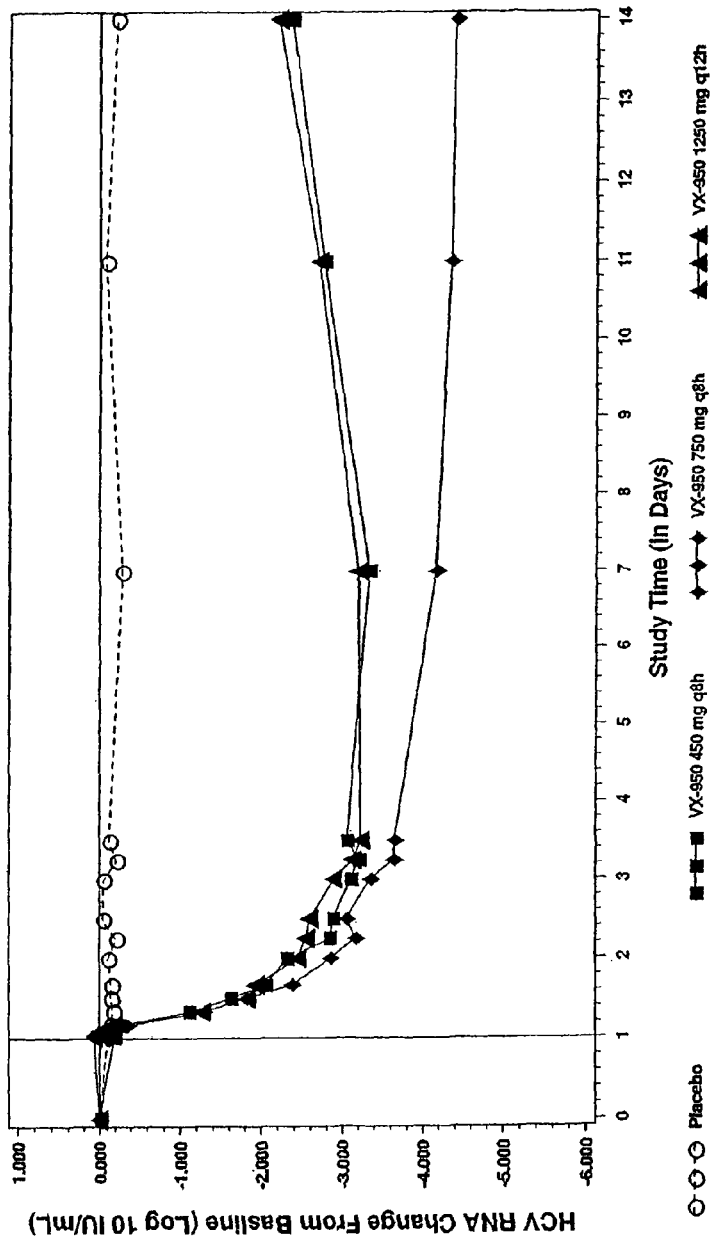

| Fold increase over WT | VX-950 | | Protease Kcat/km |
|---|---|---|---|
| | $K_i$ | $IC_{50}$ | |
| A156V | 330 | >75 | 0.25 |
| A156T | 99 | >75 | 0.1 |

Figure 14

|  | VX-950 450 mg q8h (1350 mg daily) n = 10 | VX-950 750 mg q8h (2250 mg daily) n = 8 | VX-950 1250 mg q12h (2500 mg daily) n = 10 |
|---|---|---|---|
| Mean baseline log HCV RNA | 6.42 | 6.14 | 6.41 |
| Mean log HCV RNA – IU/ml at day 7 (decline from baseline) | 3.08 (-3.33) | 2.04 (-4.10) | 3.38 (-3.03) |
| Mean log HCV RNA – IU/ml at day 14 (decline from baseline) | 3.98 (-2.43) | 1.81 (-4.33) | 4.32 (-2.09) |
| Mean baseline neopterin | 8.88 | 10.48 | 8.59 |
| Mean neopterin – nmol/l at day 7 (decline from baseline) | 7.84 (-1.05) | 8.43 (-2.04) | 7.85 (-0.74) |
| Mean neopterin – nmol/l at day 14 (decline from baseline) | 7.74 (-1.14) | 7.32* (-3.16) | 7.72 (-0.88) |
| Mean baseline ALT U/l | 71 | 52 | 66 |
| Mean ALT U/l at day 8 (decline from baseline) | 41 (-30) | 28 (-24) | 33 (-33) |
| Mean ALT U/l at day 14 (decline from baseline) | 38 (-33) | 23 (-29) | 26 (-41) |

* Decrease in the 750 mg q8h dose group is significant vs baseline value in the same group (Mann Whitney test, $P = 0.0104$) and vs the placebo group at day 14 (unpaired two-tailed T test, $P = 0.0036$)

Huh7 cells with IFNβ-Luc and NS3•4A
IFNβ induction after Sendai virus stimulation

Addition of VX-950

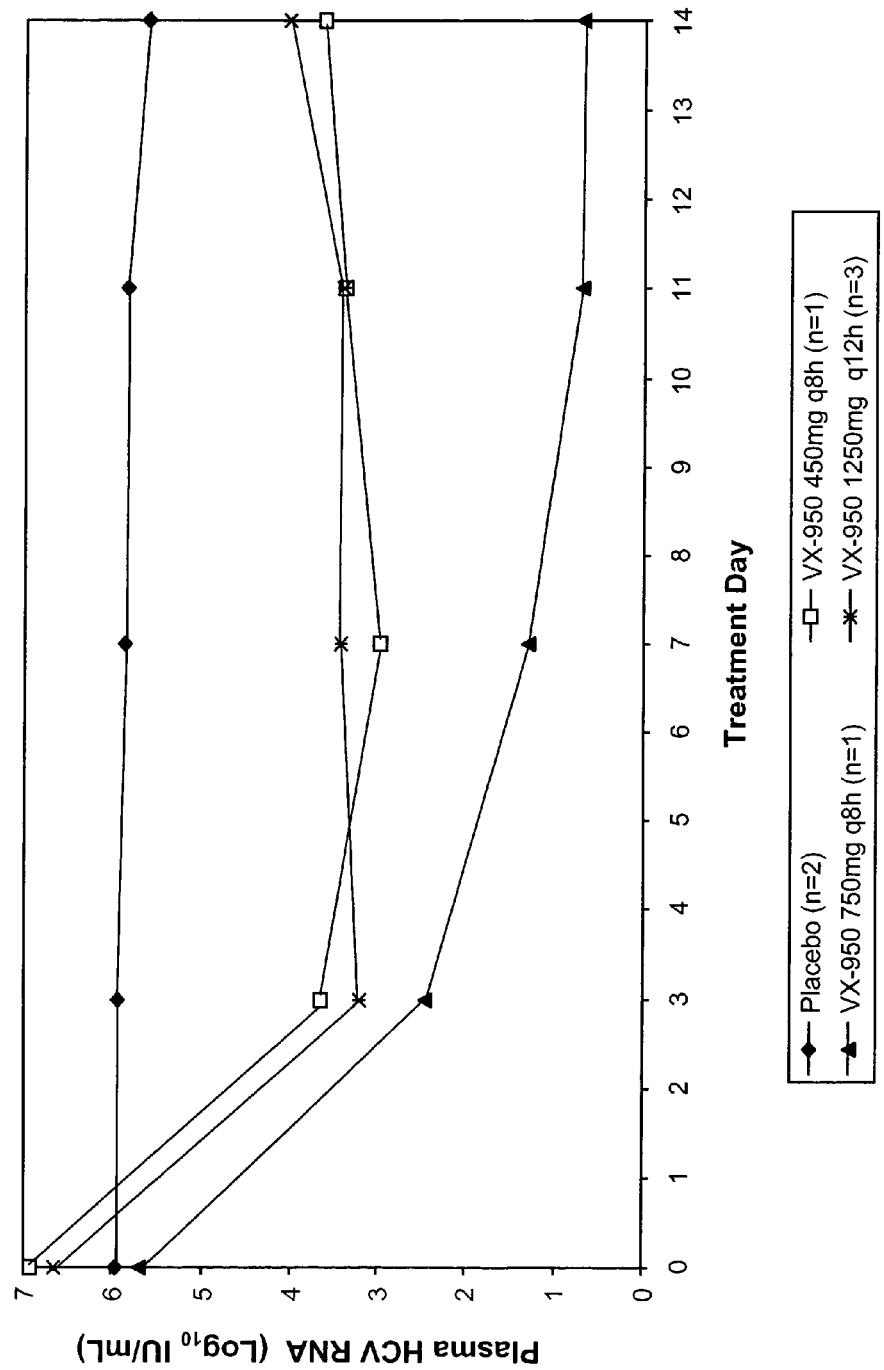

DOSE FORMS

CROSS-REFERENCE TO RELATED APPLICATIONS

This non-provisional patent application claims the benefit of U.S. Provisional Application No. 60,722,746, filed Sep. 30, 2005; U.S. Provisional Application No. 60/682,091, filed May 17, 2005; U.S. Provisional Application No. 60/679,402, filed May 9, 2005; U.S. Provisional Application No. 60/623,542, filed Oct. 29, 2004; each of which is incorporated by reference in its entirety.

TECHNICAL FIELD OF THE INVENTION

The present invention relates to methods for treating Hepatitis C virus infections.

BACKGROUND OF THE INVENTION

Infection by Hepatitis C virus ("HCV") is a compelling human medical problem. HCV is recognized as the causative agent for most cases of non-A, non-B hepatitis, with an estimated human sero-prevalence of 3% globally [A. Alberti et al., "Natural History of Hepatitis C," *J. Hepatology*, 31., (Suppl. 1), pp. 17-24 (1999)]. Nearly four million individuals may be infected in the United States alone [M. J. Alter et al., "The Epidemiology of Viral Hepatitis in the United States, *Gastroenterol. Clin. North Am.*, 23, pp. 437-455 (1994); M. J. Alter "Hepatitis C Virus Infection in the United States," *J. Hepatology*, 31., (Suppl. 1), pp. 88-91 (1999)].

Of persons who become infected with HCV, 20-25% may be able to clear the virus after the acute infection, but 75-80% will develop chronic Hepatitis C infection. [preface, *Frontiers in Viral Hepatitis*. Ed. R F Schinazi, J-P Sommadossi, and CM Rice. p. xi. Elsevier (2003)]. This usually results in recurrent and progressively worsening liver inflammation, which often leads to more severe disease states such as cirrhosis and hepatocellular carcinoma [M. C. Kew, "Hepatitis C and Hepatocellular Carcinoma", *FEMS Microbiology Reviews*, 14, pp. 211-220 (1994); I. Saito et. al., "Hepatitis C Virus Infection is Associated with the Development of Hepatocellular Carcinoma," *Proc. Natl. Acad. Sci. USA*, 87, pp. 6547-6549 (1990)]. Unfortunately, there are no broadly effective treatments for the debilitating progression of chronic HCV.

The HCV genome encodes a polyprotein of 3010-3033 amino acids [Q. L. Choo, et. al., "Genetic Organization and Diversity of the Hepatitis C Virus." *Proc. Natl. Acad. Sci. USA*, 88, pp. 2451-2455 (1991); N. Kato et al., "Molecular Cloning of the Human Hepatitis C Virus Genome From Japanese Patients with Non-A, Non-B Hepatitis," *Proc. Natl. Acad. Sci. USA*, 87, pp. 9524-9528 (1990); A. Takamizawa et. al., "Structure and Organization of the Hepatitis C Virus Genome Isolated From Human Carriers," *J. Virol.*, 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et. al., "Nonstructural Protein 3 of the Hepatitis C Virus Encodes a Serine-Type Proteinase Required for Cleavage at the NS3/4 and NS4/5 Junctions," *J. Virol.*, 67, pp. 3835-3844 (1993); A. Grakoui et. al., "Characterization of the Hepatitis C Virus-Encoded Serine Proteinase: Determination of Proteinase-Dependent Polyprotein Cleavage Sites," *J. Virol.*, 67, pp. 2832-2843 (1993); A. Grakoui et. al., "Expression and Identification of Hepatitis C Virus Polyprotein Cleavage Products," *J. Virol.*, 67, pp. 1385-1395 (1993); L. Tomei et. al., "NS3 is a serine protease required for processing of hepatitis C virus polyprotein", *J. Virol.*, 67, pp. 4017-4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decreases viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", *Proc. Natl. Acad. Sci. USA*, 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", J. Virol., 68, pp. 8147-8157 (1994)].

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing. HIV protease inhibitors, which inhibit viral protein processing are potent antiviral agents in man, indicating that interrupting this stage of the viral life cycle results in therapeutically active agents. Consequently it is an attractive target for drug discovery.

There are not currently any satisfactory anti-HCV agents or treatments. Until recently, the only established therapy for HCV disease was interferon treatment. The first approved therapy for HCV infection was treatment with standard (non-pegylated) interferon alfa. However, interferons have significant side effects [M. A. Wlaker et al., "Hepatitis C Virus: An Overview of Current Approaches and Progress," *DDT*, 4, pp. 518-29 (1999); D. Moradpour et al., "Current and Evolving Therapies for Hepatitis C," *Eur. J. Gastroenterol. Hepatol.*, 11, pp. 1199-1202 (1999); H. L. A. Janssen et al. "Suicide Associated with Alfa-Interferon Therapy for Chronic Viral Hepatitis," *J. Hepatol.*, 21, pp. 241-243 (1994); P. F. Renault et al., "Side Effects of Alpha Interferon," *Seminars in Liver Disease*, 9, pp. 273-277. (1989)] and interferon alfa monotherapy induces long term remission in only a fraction (~25%) of cases [O. Weiland, "Interferon Therapy in Chronic Hepatitis C Virus Infection", *FEMS Microbiol. Rev.*, 14, pp. 279-288 (1994)]. The addition of ribavirin to the treatment regimen increases response rates slightly. Recent introductions of the pegylated forms of interferon (PEG-INTRON® and PEGASYS®), which has also been combined with ribavirin have resulted in only modest improvements in remission rates and only partial reductions in side effects. The current standard of care is a treatment regimen lasting 24-48 weeks, depending on prognostic factors such as HCV genotype and demonstration of initial response to therapy. Moreover, the prospects for effective anti-HCV vaccines remain uncertain.

Thus, there is a need for anti-HCV therapies and appropriate dose regimens for anti-HCV compounds.

HCV and other diseases and disorders are associated with liver damage. There is also a need for therapies and appropriate dose regimens for treating liver damage.

SUMMARY OF THE INVENTION

The present invention provides a treatment for Hepatitis C virus infections. The invention therefore provides for the prevention of the clinical sequelae of Hepatitis C viral infections.

The present invention also provides a treatment for liver damage and liver inflammation.

BRIEF DESCRIPTION OF THE FIGURES

FIGS. 2A-2D depict derived pharmacokinetic parameters. The line inside the box represents the median, and the box represents the limits of the middle half of the data (Example 3).

FIG. 3 depicts the concentration (IU/mL) of HCV RNA in plasma over the duration of the 14-day study (Example 5).

FIG. 4 depicts the change in the concentration (IU/mL) of HCV RNA relative to baseline over the duration of the 14-day study (Example 5).

FIG. 8 (toll-IL1 receptor domain containing adaptor inducing IFN-β TRIF or TICAM-1) depicts a schematic illustration of TRIF showing various protein binding domains. TRIF cleavage by HCV NS3 protease at Cys 372 results in two fragments-ΔC340 and ΔN372 (modified from Li et al 2005, PNAS, 102, p 2992-2997).

FIG. 9 depicts the kinetics of TRIF cleavage by HCV NS3 protease. The 35S methionine labeled coupled in vitro transcription/translation product of TRIF protein (as a substrate) was incubated with 6 μM of tNS3 protease for various time points ranging from 0-240 minutes, followed by SDS-PAGE. The gel was exposed to phosphorimager to quantitate the cleavage products. Quantitation of ΔN372 cleavage product is shown in the figure as a function of time.

FIG. 10 depicts NS3 protease dependent TRIF cleavage and inhibition of TRIF cleavage by VX-950. The 35S methionine labeled coupled in vitro transcription/translation product of TRIF protein (as a substrate) was incubated with increasing concentration of tNS3 protease enzyme ranging from 0-4 μM either in the presence (Circles) or absence (Squares) of 10 μM VX-950, followed by SDS-PAGE and exposure to phosphorimager. Quantitation of the ΔN372 cleavage product is shown in the figure.

FIG. 11 depicts phenotypic characteristics of the in vitro VX-950 resistant mutants. Increased resistance conferred by A156V/T mutations to VX-950 in the in vitro enzyme reactions (Ki) or in the 2-day replicon assay ($IC_{50}$) compared to the wild type protease. The ratio Kcat/Km of the mutants compared to the wild type enzymes is shown in the table (modified from Lin et al 2005, JBC, 280, p 36784-36791).

FIG. 12 depicts cleavage of HCV 4A/B substrate by A156V/T mutants compared to the wild type (WT) NS3 protease: The 35S methionine labeled coupled in vitro transcription/translation product of inactivated HCV mutant protease fused to SEAP protein with 4A/B junction (as a substrate) in between, was incubated with various amounts of either the wild type (WT) (Squares) or A156V/T (Triangles and Circles) tNS3 protease ranging from 0.008 μM to 6 μM, followed by SDS-PAGE and exposure to phosphorimager. Quantitation of the ΔN372 cleavage product is shown in the figure.

FIG. 13 depicts cleavage of TRIF substrate by A156V/T mutants compared to the wild type (WT) NS3 protease. The 35S methionine labeled coupled in vitro transcription/translation product of TRIF (as a substrate), was incubated with various amounts of either the wild type (WT) (Squares) or A156V/T (Triangles and Circles) tNS3 protease ranging from 0.008 μM to 6 μM, followed by SDS-PAGE and exposure to phosphorimager. Quantitation of the ΔN372 cleavage product is shown in the figure.

FIG. 14 depicts mean HCV RNA, neopterin and ALT at baseline, day 7, and day 14 (Example 5).

FIG. 15 depicts suppression of IFN-β promoter activity by HCV protease in Huh7 cells stimulated with Sendai virus. Huh7 cells were cotransfected with plasmids expressing luciferase gene under the control of IFN-b promoter either with the wild type (WT) or inactivated mutant (MT) protease, followed by Sendai virus (SeV) stimulation. The fold activation of luciferase gene compared to the Sendai virus uninduced controls are shown in this figure.

FIG. 16 depicts that treatment with VX-950 is able to overcome the suppressive effect of HCV protease on the Sendai virus stimulated IFN-β promoter activity. Huh7 cells were cotransfected with plasmids expressing luciferase gene under the control of IFN-β promoter either with the wild type (WT) or inactivated mutant (MT) protease. These cells were either treated with DMSO (Control) or 10 μM VX-950. Cells were stimulated with Sendai virus (SeV) and luciferase activity was measured 16 hours post-infection. Fold activation of luciferase gene, compared to the Sendai virus uninduced controls are shown in this figure.

DETAILED DESCRIPTION OF THE INVENTION

Figure 1A:
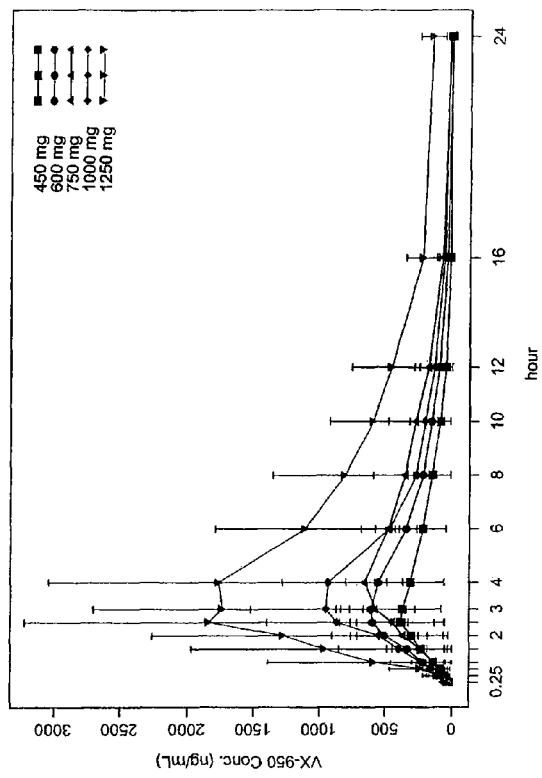
FIG. 1A AND FIG. 1B depict mean concentration time profiles by dose level (Example 3).

This invention relates to specific doses and dosage regimens for administering VX-950. VX-950 is a competitive, reversible peptidomimetic NS3/4A protease inhibitor with a steady state binding constant (ki*) of 7 nM [WO 02/018369].

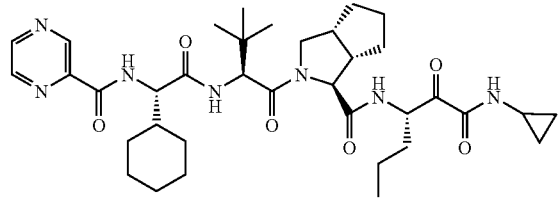 [SMILES: CCC[C@H](NC(=O)[C@@H]1[C@H]2CCC[C@H]2CN1C(=O)[C@@H](NC(=O)[C@@H](NC(=O)c1cnccn1)C1CCCCC1)C(C)(C)C)C(=O)C(=O)NC1CC1]

VX-950

VX-950 has been tested in single doses in humans and found to be well tolerated (Example 3). The incidence or severity of adverse events did not increase with VX-950 dose. No adverse events were considered to be severe (grade 3 or grade 4). There were no clinically significant changes from baseline laboratory values for hematology or clinical chemistry parameters. There were no clinically significant changes in physical examinations, vital signs, or electrocardiograms for any subject tested.

An analysis was performed to determine the pharmacokinetic profile of VX-950. The data is depicted in FIG. 1 and FIG. 2.

Liver exposures to VX-950 were predicted based on the integrated preclinical and clinical data. The predicted human liver exposures were combined with results of the VX-950 replicon assay and the infectious virus assay (see below) to determine the doses that are anticipated to be well tolerated and produce therapeutic benefit. The predicted average liver concentration values are up to 57-fold of the replicon assay $IC_{90}$ and up to 113-fold of the replicon assay $IC_{50}$ in the dose range studied.

These results indicate that the dose regimen of applicants' invention will achieve liver concentrations of VX-950 substantially in excess of the $IC_{50}$ and $IC_{90}$ determined in non-clinical studies.

Accordingly, one embodiment of this invention provides pharmaceutical compositions comprising:
a) VX-950, or a pharmaceutically acceptable salt thereof:
   in an amount of about 100 mg to about 1500 mg;
   in an amount of about 300 mg to about 1500 mg;
   in an amount of about 300 mg to about 1250 mg;
   in an amount of about 450 mg;
   in an amount of about 750 mg; or
   in an amount of about 1250 mg; and
b) and pharmaceutically acceptable carrier.

Also provided by this invention is a therapeutic regimen comprising administering VX-950, or a pharmaceutically acceptable salt thereof:
   in an amount of about 100 mg to about 1500 mg;
   in an amount of about 300 mg to about 1500 mg;
   in an amount of about 300 mg to about 1250 mg;
   in an amount of about 450 mg;
   in an amount of about 750 mg; or
   in an amount of about 1250 mg; wherein the amount is administered once, twice, or three times per day. A therapeutic regimen according to this invention is intended to include the administration of VX-950 in one or more dosage forms.

Another embodiment of this invention provides a method for treating or preventing a HCV infection a patient comprising administering to the patient VX-950, or a pharmaceutically acceptable salt thereof, in an amount of about 300 mg to about 1500 mg.

In certain embodiments, the dose of VX-950 is at least about 300 mg. In other embodiments, the dose of VX-950 is at least about 450 mg. In other embodiments, the dose of VX-950 is at least about 500 mg. In other embodiments, the dose of VX-950 is at least about 750 mg. In other embodiments, the dose of VX-950 is at least about 1250 mg. In other embodiments, the dose of VX-950 is at least about 1500 mg.

In yet other embodiments, the dose of VX-950 is no more than about 1500 mg. In other embodiments, the dose of VX-950 is no more than about 1250 mg. In other embodiments, the dose of VX-950 is no more than about 750 mg. In other embodiments, the dose of VX-950 is no more than about 450 mg. In other embodiments, the dose of VX-950 is no more than about 500 mg. In other embodiments, the dose of VX-950 is no more than about 300 mg.

It should be understood that these lower and upper amounts may be combined to provide preferred dose ranges for administering VX-950. For example, in one embodiment, the VX-950, or the pharmaceutically acceptable salt thereof, is in an amount of about 300 mg to about 1250 mg.

In certain embodiments, VX-950 is administered in an amount of about 450 mg. VX-950 is administered in an amount of about 500 mg. In other embodiments, VX-950 is administered in an amount of about 600 mg. In other embodiments, VX-950 is administered in an amount of about 750 mg. In other embodiments, VX-950 is administered in an amount of about 1000 mg. In yet other embodiments, VX-950 is administered in an amount of about 1250 mg.

In any of these embodiments, the amount of VX-950 is administered once a day. Alternatively, the amount of VX-950 is administered twice a day (e.g., BID; q12h). Alternatively, the amount of VX-950 is administered three-times per day (e.g., TID; q8h). VX-950 may be administered with or without food.

VX-950 has also been tested in humans and found to be effective at inhibiting HCV replication. Applicants have demonstrated that administration of VX-950 was able to substantially decrease HCV RNA levels. Importantly, applicants have demonstrated that administration of VX-950 to subjects infected with HCV can inhibit the virus such that the viral RNA becomes undetectable using the Roche COBAS Taq-Man™ HCV/HPS assay (available from Roche Molecular Diagnostics). Of the 8 subjects receiving 750 mg of VX-950 every 8 hours (q8h), 4 had HCV RNA levels below the limit of quantitation (LLQ 30 IU/mL) and 2 of those 4 subjects had HCV RNA levels below the limit of detection (LLD 10 IU/mL).

Figure 5:
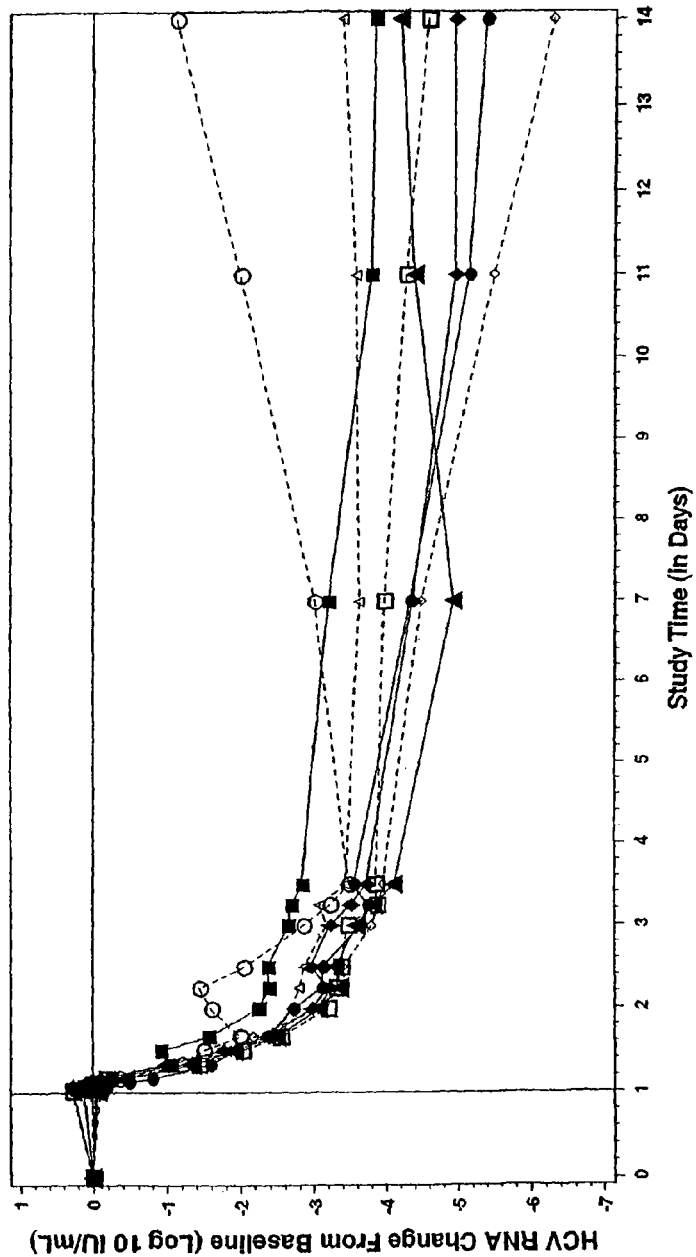
FIG. 5 depicts the change in the concentration (IU/mL) of HCV RNA relative to baseline over the duration of the 14-day study for individual subjects in the 750 mg q8h dose group (Example 5).

Subjects receiving 750 mg of VX-950 every eight hours achieved a median reduction in HCV-RNA of greater than 4 $log_{10}$ (i.e., 10,000-fold decrease) at the end of 14 days of treatment. A median reduction of HCV-RNA of greater than 2 $log_{10}$ was seen in each of the other two VX-950 dose groups at the end of 14 days of treatment. Every subject receiving VX-950 achieved greater than a 2 $log_{10}$ reduction in HCV-RNA within the first three days of treatment, and 26 of the 28 subjects receiving VX-950 had a 3 $log_{10}$ reduction in HCV-RNA within the first three days of treatment. See, Example 5 and FIGS. 3-5.

It was demonstrated that plasma viral loads decline rapidly in patients treated with VX-950. Additionally, it was demonstrated that there was a slow return towards baseline HCV RNA levels after the end of dosing. Specifically, the rate of return to HCV RNA baseline levels following the end of treatment was slower than the rate of decline of HCV RNA upon treatment. These results together with achieving undetectable HCV RNA levels, indicate the effectiveness of VX-950 as a monotherapy.

Accordingly, this invention provides a method for treating a patient infected with HCV, comprising administering to the patient VX-950, or a pharmaceutically acceptable salt thereof, in an amount of: a) about 450 mg, 3 times per day, every 8 hours; b) about 750 mg, 3 times per day, every 8 hours; c) about 1250 mg, 2 times per day, every 12 hours; or d) about 1250 mg, 3 times per day, every 8 hours.

In other embodiments, this invention provides a method for administering VX-950 to a patient infected with HCV, such that the level of HCV RNA in the patient is at least about 2 log (preferably at least about 4 log) lower after treatment than before treatment. In another embodiment, this invention provides a method for administering VX-950 to a patient infected with HCV, such that the level of viral RNA in the patient is decreased to undetectable levels and remains at undetectable levels until a "sustained viral response" is achieved. As is currently defined, "sustained viral response" means that 24 weeks after dosing is completed, viral RNA levels remain undetectable.

Without being bound by theory, it is thought that a method of this invention that employs 750 mg of VX 950 every 8 hours is preferred because the method results in higher trough levels. The trough level is the concentration that a drug drops down to in plasma just before next dose (i.e., the minimum concentration between doses). It is important, particularly in viral diseases, to maintain drug levels above a certain concentration to maintain appropriate inhibition of viral replication. Advantageously, applicants have found that one regimen, administering 750 mg of VX-950, every 8 hours, led to the highest trough levels of the tested regimens.

Accordingly, in a preferred embodiment, this invention provides a method comprising administering to a patient VX-950, or a pharmaceutically acceptable salt thereof, in an amount of about 750 mg, 3 times per day, every 8 hours.

As would be recognized, it advantageous to have flexible dosing schedules. Accordingly, in another embodiment of this invention, the administration is 3 times per day, but not every 8 hours, optionally with meals. In certain embodiments, VX-950 is administered with food.

This invention also provides a method for providing VX-950 to a human in need thereof, comprising administration to the human an oral dose of a composition comprising VX-950, wherein said dose provides to said human an average plasma concentration ($C_{avg}$) of VX-950 of at least about 750 ng/mL after the administration. In certain embodiments, the ($C_{avg}$) is about 1000 ng/mL or about 1250 ng/ml. In certain embodiments, said dose essentially contains 750 mg of VX-950. In these embodiments, the ($C_{avg}$) is obtained/attained within 3 hours after administration, preferably 2 hours, more preferably 1 hour after administering. In a preferred form of these embodiments, the ($C_{avg}$) is maintained over about 24 hours, and preferably over 12 weeks.

In certain embodiments, this invention provides a method for treating HCV infection in a patient by administering at least one dosage form comprising VX-950 over a 24 hour period, wherein the dosage form is administered to maintain a trough plasma VX-950 level minimum of about 750 ng/mL over the 24 hour period.

In certain forms of this embodiment, the dosage form is administered to maintain a trough plasma VX-950 level minimum of about 800 ng/mL, preferably about 900 ng/ml over the 24 hour period, and more preferably about 1000 ng/mL over the 24 hour period.

In certain preferred embodiments a therapeutically effective plasma concentration is obtained and a certain trough level is maintained. These methods are particularly useful for treating a human suffering from HCV infection by administering a VX-950 formulation, wherein the trough VX-950 plasma level is maintained at a minimum of about 750, 800, 900, or 1000 ng/mL over a 24 hour period. Without being bound by theory, trough levels of more than about 1500 ng/mL are thought to be not required by this invention. Accordingly, trough levels of about 750, 800, 900, 1000 ng/mL to about 1500 ng/mL (particularly 1000 to about 1500) are within the scope of this invention.

Also provided is a dosage form for delivering VX-950 to a human, wherein the dosage form comprises VX-950, said dosage form when administered at least once during a 24 hour period maintains a trough plasma VX-950 level that is at least about 750 ng/mL, 800 ng/mL, 900 ng/mL, or 1000 ng/mL over the 24 hour period to about 1500 ng/mL (particularly 1000 ng/mL to about 1500 ng/mL) over the 24 hour period.

Ideally, when a method of this invention involves treating a patient infected with HCV, the method involves achieving, relatively rapidly, a therapeutically effective plasma concentration of VX-950 and then maintaining the trough level such that an effective therapeutic response is achieved. An effective therapeutic response is, preferably, one or both of a) achieving a sustained viral response; and b) achieving undetectable HCV RNA in the plasma by at least 12 weeks (12 weeks or more). As used herein, HCV RNA being "undetectable" means that the HCV RNA is present in less than 10 IU/ml as determined by assays currently commercially available, and preferably as determined by the Roche COBAS TaqMan™ HCV/HPS assay.

The relatively rapid drop in plasma concentration may be obtained by administering a loading dose to a patient. In one embodiment, the loading dose is about 1250 mg of VX-950.

In certain dosage forms of this invention, the dosage form (other than the dosage form used to administer the loading dose) contains about 750 mg of VX-950 and the dosage form is administered three times in each 24 hour period.

In certain embodiments, the treatment duration with VX-950 is shorter than the current standard of care.

In certain embodiments, a method according to this invention involves the treatment of a patient infected with genotype 1 Hepatitis C virus. Genotype 1 HCV infection is the most difficult strain of HCV to treat and the most prevalent strain in the United States.

Figure 6:
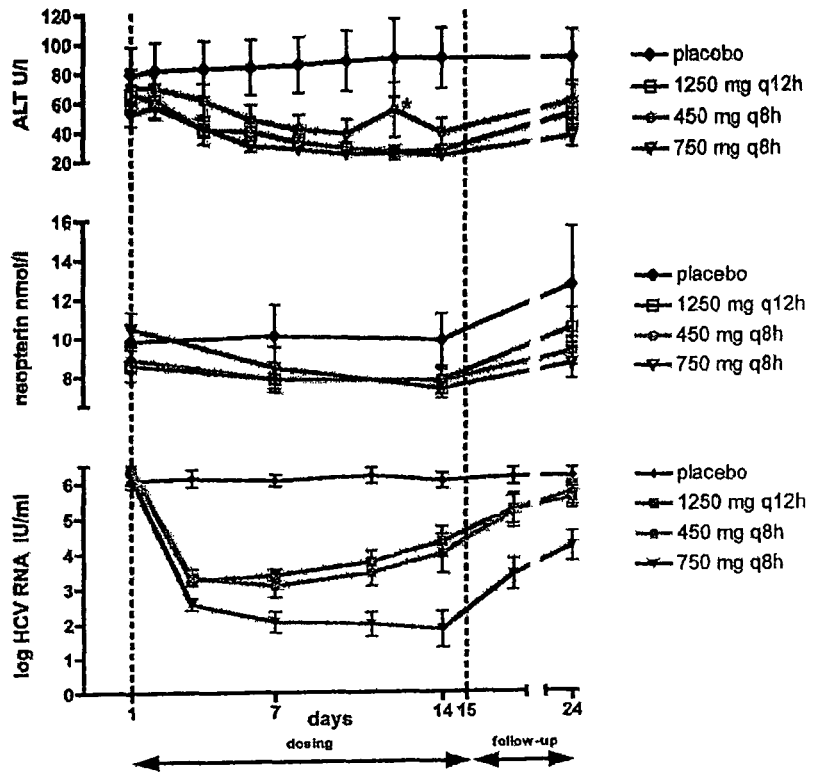
FIG. 6 depicts mean neopterin, ALT (alanine aminotransferase), and HCV RNA +/−SEM in all dose groups. The following symbols are used in FIG. 6: Changes from baseline in mean ALT levels ±SEM (uppermost 4 lines with open symbols), mean plasma neopterin levels ±SEM (middle 4 lines with open symbols) and mean plasma HCV RNA loads ±SEM (lower 4 lines, closed symbols) are shown for all 3 dose groups and placebo. Patients were treated for 14 days with VX-950. *The transient increase in mean ALT level at day 12 in the 450 mg q8h group is an artifact (5 out of 10 samples were missing, median value 38 U/l, range 25-125 U/l) (Example 5).
Figure 7:
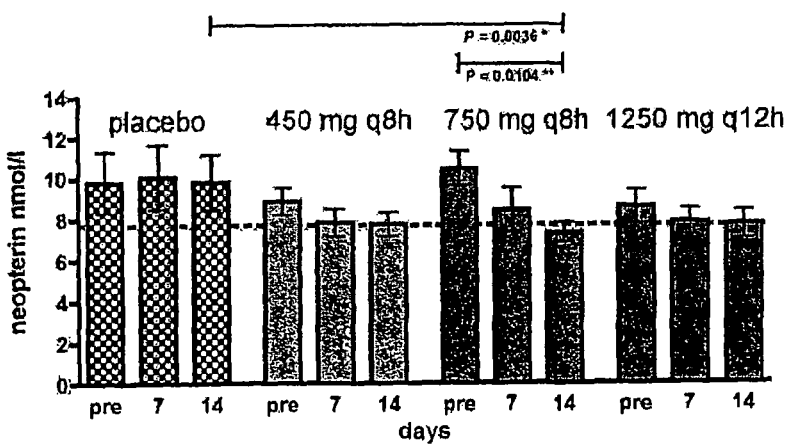
FIG. 7 depicts mean neopterin values +/−SEM in all groups. Mean plasma neopterin levels ±SEM pretreatment and at days 7 and 14 for all 3 dose groups and placebo. Note that decrease in mean neopterin is greatest in the 750 mg q8h dose group, with the highest pretreatment values and then the lowest mean values at day 14. In the 750 mg q8h dose group the decrease in neopterin compared to baseline and to placebo became significant at day 14 (*unpaired two-tailed T test, **Mann Whitney test). The broken horizontal line at Y=7.7 nmol/l represents the ULN (Example 5).

Applicants have also demonstrated that administration of VX-950 decreases neopterin and ALT levels in vivo (FIG. 6, FIG. 7, & FIG. 14). AST (aspartate aminotransferase) levels were also decreased upon administration of VX-950. ALT is an enzyme that is present in liver cells; when liver cells are damaged or inflamed, ALT leaks from the cell into the blood. Blood ALT levels are useful as a marker of liver inflammation or damage. See, Tatyana Yashina & J. Sanders Sevall, "Hepatitis C Virus" in *Use and Interpretation of Laboratory Tests in Gastroenterology*, James B. Peter, ed., p. 127, (1998); and Andres T. Blei, "Liver and Biliary Tract" in *Laboratory Medicine*, D. A. Noe and Robert C. Rock, eds., ch. 19, p. 363 (1994).

Neopterin (6-d-erythro-trihydroxypropylpteridine) is a pteridine derivative that is produced during the metabolism of guanosine triphosphate (GTP). Neopterin is produced primarily by monocytes and macrophages upon activation by interferon gamma or interferon alfa and is a marker of inflammation. Neopterin levels are frequently elevated in chronic HCV infection (Quiroga, et al. Dig Dis Sci 1994; 39(11): 2485-96).

The expected plasma level of neopterin in healthy individuals is between 3.1 and 7.7 nmol/l.

Accordingly, applicants determined the changes in serum neopterin concentration as a marker of monocyte/macrophage activity during administration of an inhibitor of (HCV) NS3·4A protease. As described herein, VX-950 was administered for 14 days in a randomized, double blind, placebo controlled, multiple-dose study in 34 patients infected with HCV genotype 1 (Table 1). Patients received VX-950 450 mg q8h (n=10), 750 mg q8h (n=8), 1250 mg q12h (n=10), or placebo (n=6). Serum neopterin concentrations were measured by a quantitative competitive ELISA (ELItest® Neopterin, Brahms, Hennigsdorf, Germany) at pretreatment, at day 7 and 14, and at day 10 of follow-up. The lower limit of detection (LLD) was 2 nmol/l. HCV RNA was assessed at frequent intervals during the study by real-time PCR (CO-BAS® TaqMan HCV Test; linear dynamic range of $3.0 \times 10^1$ to $2.0 \times 10^8$ HCV RNA IU/ml; LLD of 10 HCV RNA IU/ml; Roche Diagnostics, Branchburg, N.J.).

Figure 17A:
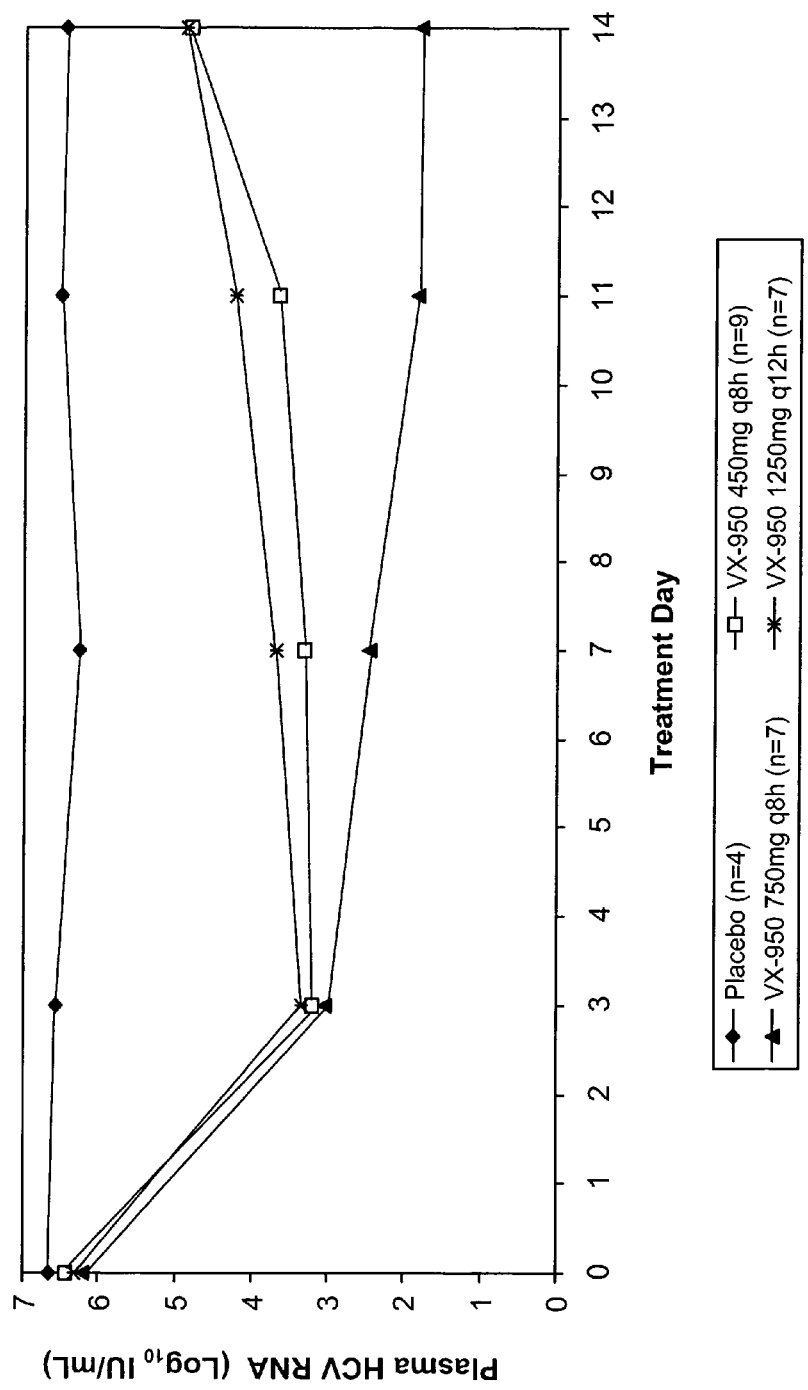
FIG. 17 depicts data that VX-950 treatment leads to decreases in HCV RNA in previous nonresponders to HCV therapy (FIG. 17A) and treatment-naïve Patients (FIG. 17B). Median HCV RNA levels of patients in each treatment regimen are shown. Plasma HCV RNA concentrations were determined using the Roche COBAS TaqMan HCV/HPS assay.

During administration of VX-950, every patient demonstrated a >2-$\log_{10}$ drop in viral load in all dose groups (Table 2). In the 750 mg q8h dose group, mean HCV RNA dropped 3.6 $\log_{10}$ at day 3, and 4.3 $\log_{10}$ at day 14. In the 450 mg q8h and 1250 mg q12h dose groups, maximal effect was seen at day 3 to day 7 followed by an increase in mean viral load between day 7 and day 14. Mean viral loads increased in all dose groups during follow-up. Advantageously, both HCV treatment naïve and previously treated patients benefit from the methods of this invention. As depicted in FIG. 17A and FIG. 17B, both prior-treated patients and treatment naïve patients responded to VX-950. For the avoidance of doubt, patients that may be treated according to the methods of this invention include those where HCV treatment has not been tried or has failed, including non-responding, rebound, relapse, and breakthrough patients.

Baseline neopterin was elevated in 23/34 patients (mean 9.33 nmol/l; upper limit of normal (ULN) 7.7 nmol/l). In the 750 mg dose group the decrease in neopterin compared to baseline and to placebo became significant at day 14 (750 mg q8h dose group baseline v day 14 10.48±0.84 nmol/l v 7.32±0.48 nmol/l P=0.0104, Mann Whitney test; 750 mg q8h dose group v placebo day 14 7.32±0.48 nmol/l v 9.81±1.36 nmol/l P=0.0036, unpaired two-tailed T test). Mean neopterin levels were within normal values at day 14 only in the 750 mg q8h dose group (FIG. 7 and FIG. 14). In the 450 mg q8h dose group and the 1250 mg q12h dose group, decreases in mean neopterin levels were smaller (FIGS. 6, 7, and 14). Mean neopterin levels did not change in the placebo group (FIG. 6 and FIG. 7). Mean neopterin levels increased in all dose groups during follow-up.

Mean ALT levels, elevated at baseline, decreased during dosing in all groups (FIG. 6). Mean ALT levels increased, returned toward baseline, in all dose groups during follow up.

Although HCV RNA increased in the 450 mg dose group and 1250 mg dose group after day 7, neopterin and especially ALT continued to decrease. Changes in mean neopterin concentration correlated with decline in HCV RNA and ALT levels during dosing of VX-950. Maximal decline in mean neopterin concentration was in the 750 mg q8h dose group at day 14. This was also the dose group with maximal reductions in HCV RNA at day 14. After day 7 in the 450 mg q8h and 1250 mg q12h dose groups, ALT and neopterin levels decreased while HCV RNA levels increased. These data suggest that inhibition of HCV replication by VX-950 results in a marked decline in systemic inflammatory activity associated with viral infection.

VX-950 also ameliorates elevated ALT levels in an animal model (see WO 2005/025517). Specifically, expression of WT-HCV protease-SEAP in SCID mice results in elevated ALT levels that can be ameliorated by treatment with VX-950. Expression of WT-HCV protease alone in SCID mice also results in time and dose dependent elevation of ALT levels.

Accordingly, another embodiment of this invention provides methods for treating or preventing one or more of liver damage, liver inflammation, steatosis, fatty liver, NAFLD, NASH, alcoholic steatosis, and Reye's syndrome in a patient that is either HCV positive or HCV negative. The invention also provides methods for hepatoprotection in a patient that is either HCV positive or negative.

Applicants have also demonstrated that VX-950 blocks immune evasion in in vitro.

Figure 15:
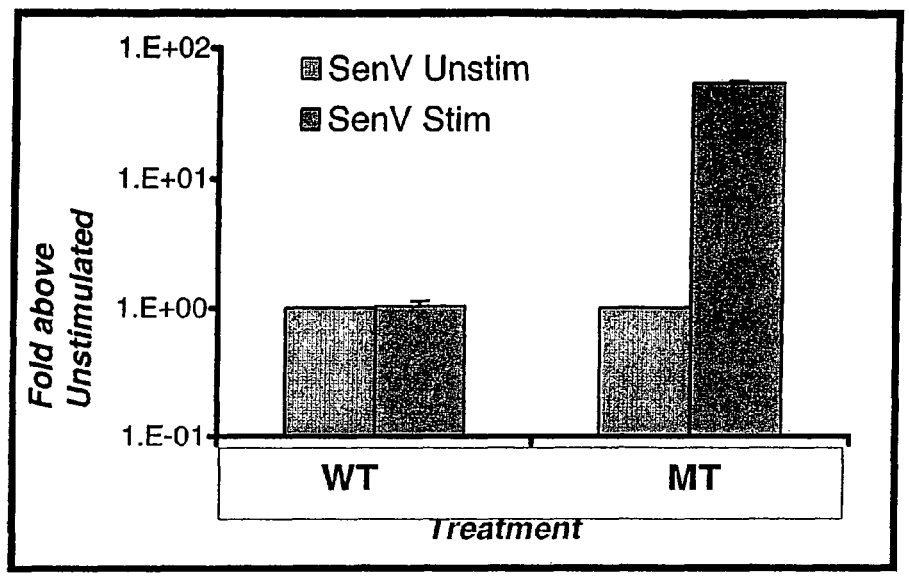
FIGS. 15 and 16 depicts data that VX-950 restores IFNβ dependent gene expression in Sendai virus infected Huh7 cells.
Figure 16:
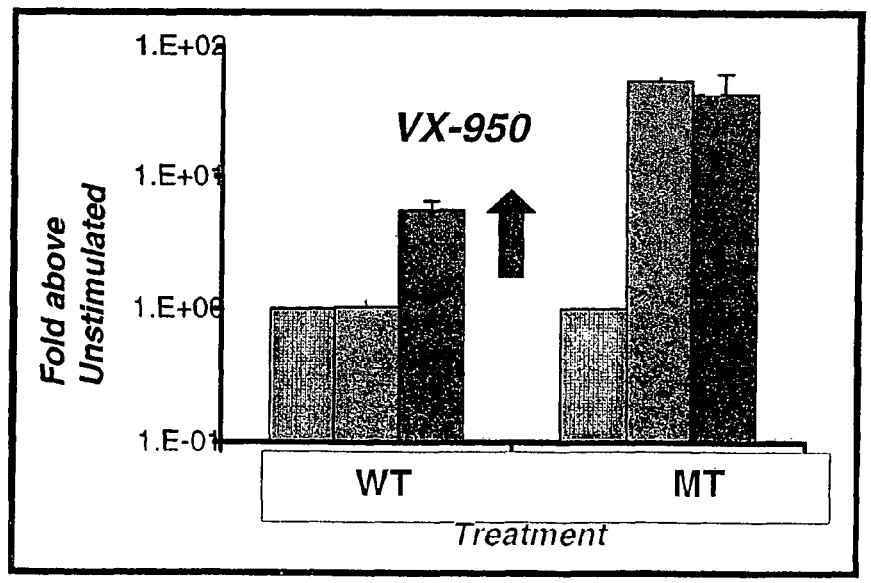

VX-950 restores IFNβ dependent gene expression in Sendai virus infected Huh7 cells. IFNβ promoter activity decreases in response to Sendai virus stimulation in the presence of WT HCVpro. VX-950 overcomes the WT HCVpro mediated suppression of IFNβ promoter activation. FIG. 15 and FIG. 16.

Figure 8:
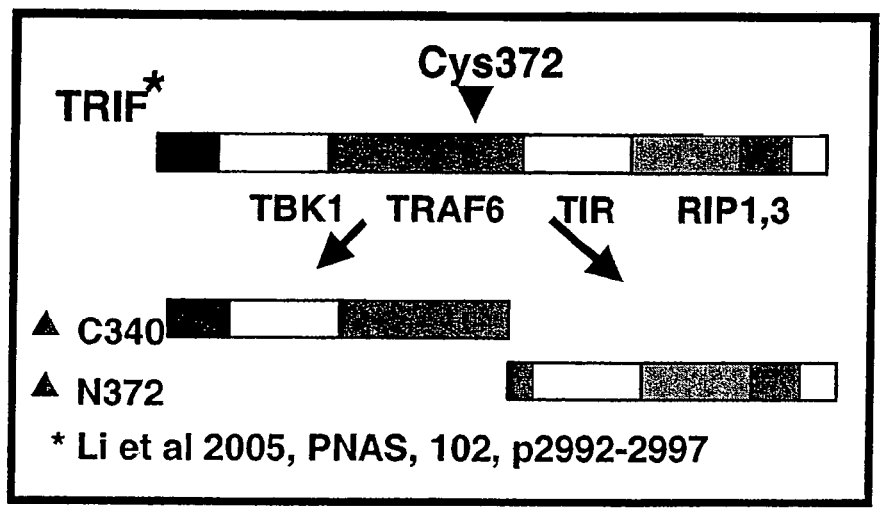
FIGS. 8, 9, and 10 depict that in vitro cleavage of TRIF (a TLR3 adaptor protein) by HCV NS3/4A protease is inhibited by VX-950.
Figure 9:
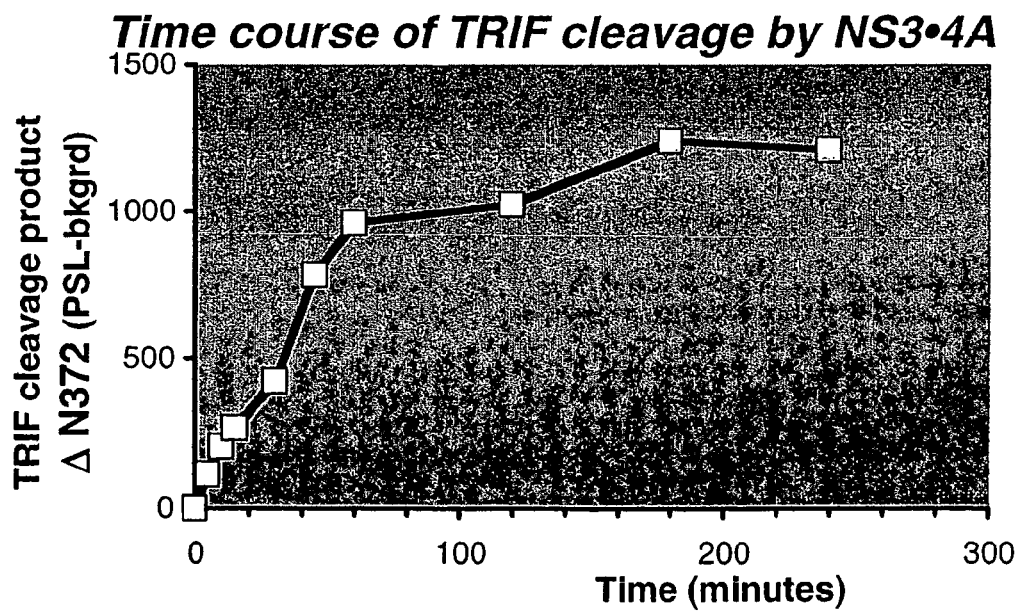
Figures 10, 11:
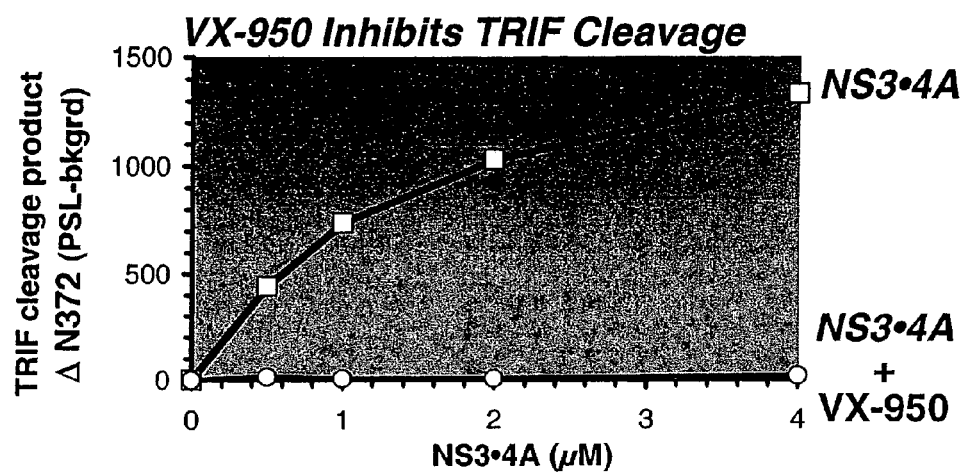
FIGS. 11, 12, and 13 depict decreased fitness of viral variants.

Furthermore, NS3/4A is known to be involved in evasion of innate defenses, by e.g., TRIF-dependent mechanisms (as well as viral polyprotein processing). This immune evasion leads to viral persistence. Accordingly, a compound that inhibits both viral polyprotein processing and evasion of innate defenses is desirable. Advantageously, VX-950 has been shown to do both. In particular, VX-950 inhibits in vitro cleavage of TRIF, which is a TLR3 adaptor protein. FIGS. 8-10

Without being bound by theory, modeling suggests that VX-950 inhibits TRIF cleavage by NS3 protease. TRIF binds to non-prime side of the NS3 protease active site. VX-950 binds to the same non-prime side of the active site as TRIF and blocks TRIF cleavage.

Figure 12:
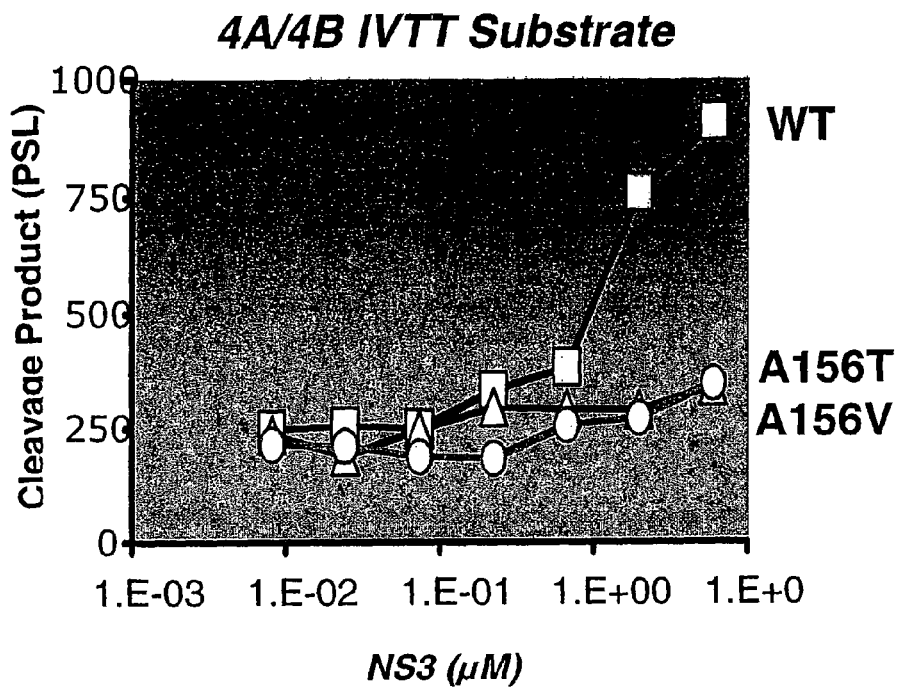
Figure 13:
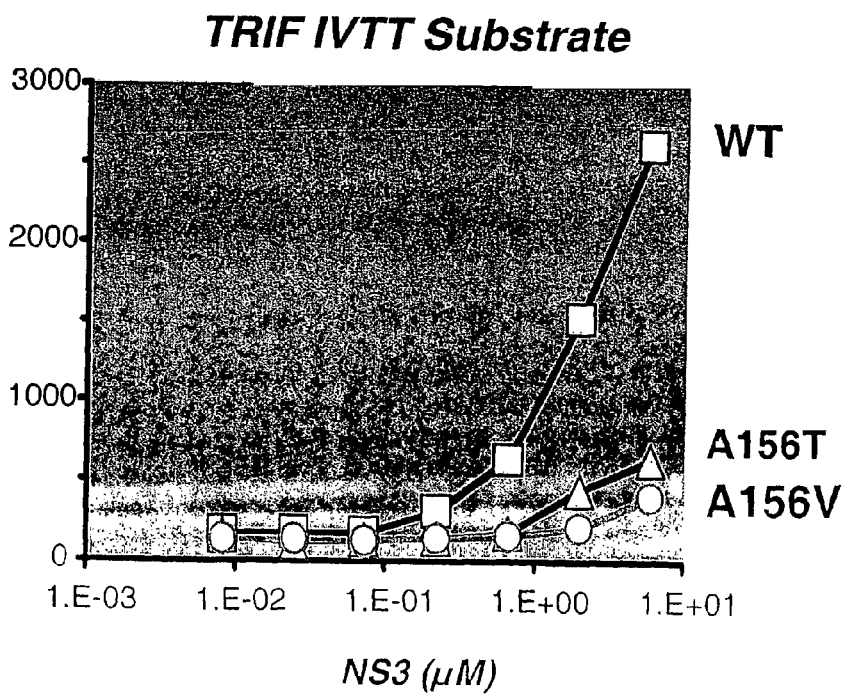

Additionally, applicants have shown that two VX-950 viral variants, A156T and A156V, show reduced ability to cleave either TRIF or 4A/4B (C. Lin et al. "In Vitro Studies of Cross-resistance Mutations Against two Hepatitis C Virus Serine Protease Inhibitors VX-950 and BILN 2061", *J. Biol. Chem.*, (Aug. 8, 2005). Because these viral variants are less fit, they are inefficient at both viral polyprotein processing and viral persistence. Without being bound by theory, this is related to steric hindrance of A156V affecting binding to 4A/4B & TRIF substrates. FIGS. 11-13.

This indicates that VX-950 acts as both a direct antiviral and as an inhibitor of immune evasion. Accordingly, this invention also provides methods of inhibiting HCV protease mediated evasion of host defenses.

These results together with the in vivo data disclosed herein indicate the effectiveness of VX-950 as a monotherapy.

The amounts of VX-950 according to this invention are administered in a single dosage form or in more than one dosage form. If in separate dosage forms, each dosage form is administered about simultaneously. For the avoidance of doubt, for dosing regimens calling for dosing more than once a day, one or more pill or dose may be given at each time per day (e.g., 1 pill, three times per day or 3 pills, three times per day). Most embodiments of this invention will employ at least 2 pills per dose).

VX-950 may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration. The D- and L-isomers at the N-propyl side chain of VX-950 are expressly included within this invention. Preferred embodiments of this invention employ VX-950.

As would be realized by skilled practitioners, if a method of this invention is being used to treat a patient prophylactically, and that patient becomes infected with Hepatitis C virus, the method may then treat the infection. Therefore, one embodiment of this invention provides methods for treating or preventing a Hepatitis C infection in a patient.

In addition to treating patients infected with Hepatitis C, the methods of this invention may be used to prevent a patient from becoming infected with Hepatitis C. Accordingly, one embodiment of this invention provides a method for preventing a Hepatitis C virus infection in a patient comprising administering to the patient a composition or dosage form according to this invention.

Methods of this invention may also involve administration of another component comprising an additional agent selected from an immunomodulatory agent; an antiviral agent; an inhibitor of HCV protease (other than VX-950); an inhibitor of another target in the HCV life cycle (other than NS3/4A protease); an inhibitor of internal ribosome entry, a broad-spectrum viral inhibitor; or a cytochrome P-450 inhibitor; or combinations thereof. The additional agent is also selected from an inhibitor of viral cellular entry.

Accordingly, in another embodiment, this invention provides a method comprising administering VX-950 and another anti-viral agent, preferably an anti-HCV agent. Such anti-viral agents include, but are not limited to, immunomodulatory agents, such as α-, β-, and γ-interferons or thymosin, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase, polymerase, and metalloprotease inhibitors; inhibitors of internal ribosome entry; broad-spectrum viral inhibitors, such as IMPDH inhibitors (e.g., compounds of U.S. Pat. Nos. 5,807,876, 6,498,178, 6,344,465, 6,054,472, WO 97/40028, WO 98/40381, WO 00/56331, and mycophenolic acid and derivatives thereof, and including, but not limited to VX-497, VX-148, and/or VX-944); or combinations of any of the above.

Other agents (e.g., non-immunomodulatory or immunomodulatory compounds) may be used in combination with a compound of this invention include, but are not limited to, those specified in WO 02/18369, which is incorporated herein by reference (see, e.g., page 273, lines 9-22 and page 274, line 4 to page 276, line 11 this disclosure being specifically incorporated herein by reference).

Still other agents include those described in various published U.S. Patent Applications. These publications provide additional teachings of compounds and methods that could be used in combination with VX-950 in the methods of this invention, particularly for the treatment of hepatitis. It is contemplated that any such methods and compositions may be used in combination with the methods and compositions of the present invention. For brevity, the disclosure the disclosures from those publications is referred to be reference to the publication number but it should be noted that the disclosure of the compounds in particular is specifically incorporated herein by reference. Exemplary such publications include U.S. Patent Publication No. 20040058982; U.S. Patent Publication No. 20050192212; U.S. Patent Publication No. 20050080005; U.S. Patent Publication No. 20050062522; U.S. Patent Publication No. 20050020503; U.S. Patent Publication No. 20040229818; U.S. Patent Publication No. 20040229817; U.S. Patent Publication No. 20040224900; U.S. Patent Publication No. 20040186125; U.S. Patent Publication No. 20040171626; U.S. Patent Publication No. 20040110747; U.S. Patent Publication No. 20040072788; U.S. Patent Publication No. 20040067901; U.S. Patent Publication No. 20030191067; U.S. Patent Publication No. 20030187018; U.S. Patent Publication No. 20030186895; U.S. Patent Publication No. 20030181363; U.S. Patent Publication No. 20020147160; U.S. Patent Publication No. 20040082574; U.S. Patent Publication No. 20050192212; U.S. Patent Publication No. 20050187192; U.S. Patent Publication No. 20050187165; U.S. Patent Publication No. 20050049220; and U.S. Patent Publication No. US2005/0222236.

Still other agents include, but are not limited to, Albuferonlm (albumin-Interferon alpha) available from Human Genome Sciences; PEG-INTRON® (peginterferon alfa-2b, available from Schering Corporation, Kenilworth, N.J.); INTRON-A®, (VIRAFERON®, interferon alfa-2b available from Schering Corporation, Kenilworth, N.J.); ribavirin (1-beta-D-ribofuranosyl-1H-1,2,4-triazole-3-carboxamide, available from ICN Pharmaceuticals, Inc., Costa Mesa, Calif.; described in the Merck Index, entry 8365, Twelfth Edition); REBETROL® (Schering Corporation, Kenilworth, N.J.); COPEGUS® (Hoffmann-La Roche, Nutley, N.J.); PEGASYS® (peginterferon alfa-2a available Hoffmann-La Roche, Nutley, N.J.); ROFERON® (recombinant interferon alfa-2a available from Hoffmann-La Roche, Nutley, N.J.); BEREFOR® (interferon alfa 2 available from Boehringer Ingelheim Pharmaceutical, Inc., Ridgefield, Conn.); SUMIFERON® (a purified blend of natural alpha interferons such as Sumiferon available from Sumitomo, Japan); WELLFERON® (interferon alpha n1 available from Glaxo Wellcome Ltd., Great Britain); ALFERON® (a mixture of natural alpha interferons made by Interferon Sciences, and available from Purdue Frederick Co., Conn.); a-interferon; natural alpha interferon 2a; natural alpha interferon 2b; pegylated alpha interferon 2a or 2b; consensus alpha interferon (Amgen, Inc., Newbury Park, Calif.); REBETRON® (Schering Plough, Interferon-alpha 2B+Ribavirin); pegylated interferon alpha (Reddy, K. R. et al. "Efficacy and Safety of Pegylated (40-kd) Interferon alpha-2a Compared with Interferon alpha-2a in Noncirrhotic Patients with Chronic Hepatitis C (*Hepatology,* 33, pp. 433-438 (2001); consensus interferon (INFERGEN®)(Kao, J. H., et al., "Efficacy of Consensus Interferon in the Treatment of Chronic Hepatitis" *J. Gastroenterol. Hepatol.* 15, pp. 1418-1423 (2000); lymphoblastoid or "natural" interferon; interferon tau (Clayette, P. et al., "IFN-tau, A New Interferon Type I with Antiretroviral activity" *Pathol. Biol.* (Paris) 47, pp. 553-559 (1999); interleukin-2 (Davis, G. L. et al., "Future Options for the Management of Hepatitis C." *Seminars in Liver Disease,* 19, pp. 103-112 (1999); Interleukin-6 (Davis et al. "Future Options for the Management of Hepatitis C." *Seminars in Liver Disease* 19, pp. 103-112 (1999); interleukin-12 (Davis, G. L. et al., "Future Options for the Management of Hepatitis C." *Seminars in Liver Disease,* 19, pp. 103-112 (1999); and compounds that enhance the development of type 1 helper T cell response (Davis et al., "Future Options for the Management of Hepatitis C." *Seminars in Liver Disease,* 19, pp. 103-112 (1999)). Also included are compounds that stimulate the synthesis of interferon in cells (Tazulakhova, E. B. et al., "Russian Experience in Screening, analysis, and Clinical Application of Novel Interferon Inducers" *J. Interferon Cytokine Res.,* 21 pp. 65-73) including, but are not limited to, double stranded RNA, alone or in combination with tobramycin, and Imiquimod (3M Pharmaceuticals; Sauder, D. N. "Immunomodulatory and Pharmacologic Properties of Imiquimod" *J. Am. Acad. Dermatol.,* 43 pp. S6-11 (2000). See also, WO 02/18369, particularly page 272, line 15 to page 273, line 8, this disclosure being specifically incorporated herein by reference.

As is recognized by skilled practitioners, VX-950 is preferably administered orally. Interferon is not typically administered orally, although orally administered forms are in development. Nevertheless, nothing herein limits the methods or combinations of this invention to any specific dosage forms or regime. Thus, each component of a combination according to this invention may be administered separately, together, or in any combination thereof. As recognized by skilled practitioners, dosages of interferon are typically measured in IU (e.g., about 4 million IU to about 12 million IU). Interferon may also be dosed by micrograms. For example, a standard dose of Peg-Intron is 1.0-1.5 μg/kg/wk and of Pegasys is 180 μg/wk.

A cytochrome P450 monooxygenase ("CYP") inhibitor used in connection with this invention is expected to inhibit metabolism of VX-950. Therefore, the cytochrome P450 monooxygenase inhibitor would be in an amount effective to inhibit metabolism of VX-950. Accordingly, the CYP inhibitor is administered in an amount such that the bioavailability of or exposure to VX-950 is increased in comparison to VX-950 in the absence of the CYP inhibitor. CYP inhibitors include, but are not limited to, ritonavir (WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methyl pyrazole, cyclosporin, and clomethiazole.

Methods for measuring the ability of a compound to inhibit cytochrome P50 monooxygenase activity are known (see, U.S. Pat. No. 6,037,157 and Yun, et al. *Drug Metabolism & Disposition*, vol. 21, pp. 403-407 (1993)). Methods for evaluating the influence of co-administration of VX-950 and a CYP inhibitor in a subject are also known (US2004/0028755). Any such methods could be used in connection with this invention to determine the pharmacokinetic impact of a combination.

One embodiment of this invention provides a method for administering an inhibitor of CYP3A4 and VX-950.

The methods herein may involve administration or co-administration of a) combinations of VX-950 and another agent; or b) VX-950 in more than one dosage form. Co-administration includes administering each inhibitor in the same dosage form or in different dosage forms. When administered in different dosage forms, the inhibitors may be administered at different times, including about simultaneously or in any time period around administration of the other dosage forms. Separate dosage forms may be administered in any order. That is, any dosage forms may be administered prior to, together with, or following the other dosage forms.

VX-950, and any additional agent, may be formulated in separate dosage forms. Alternatively, to decrease the number of dosage forms administered to a patient, VX-950, and any additional agent, may be formulated together in any combination. Any separate dosage forms may be administered at the same time or different times. It should be understood that dosage forms should be administered within a time period such that the biological effects were advantageous.

According to the regimens and dosage forms of this invention, VX-950 is present in an amount effective to decrease the viral load in a sample or in a patient, wherein said virus encodes a NS3/4A serine protease necessary for the viral life cycle (or in an amount effective to carry out a method of this invention), and a pharmaceutically acceptable carrier. Alternatively, a composition of this invention comprises an additional agent as described herein. Each component may be present in individual compositions, combination compositions, or in a single composition.

If pharmaceutically acceptable salts of compounds are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, particularly a human being.

Such pharmaceutical compositions of the present invention (as well as compositions for use in methods, combinations, kits, and packs of this inventions) may be administered orally, parenterally, sublingually, by inhalation spray, topically, rectally, nasally, buccally, vaginally or via an implanted reservoir. The term "parenteral" as used herein includes subcutaneous, intravenous, intramuscular, intra-articular, intrasynovial, intrasternal, intrathecal, intrahepatic, intralesional and intracranial injection or infusion techniques. Preferably, the compositions are administered orally or intravenously. More preferably, the compositions are administered orally.

Sterile injectable forms of the compositions of and according to this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In compositions of this invention comprising VX-950 and an additional agent, VX-950 and the additional agent should be present at dosage levels of between about 10 to 100%, and more preferably between about 10 to 80% of the dosage normally administered in a monotherapy regimen.

The pharmaceutical compositions of this invention may be orally administered in any orally acceptable dosage form including, but not limited to, capsules, tablets, pills, powders, granules, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. Acceptable liquid dosage forms include emulsions, solutions, suspensions, syrups, and elixirs.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

As is recognized in the art, pharmaceutical compositions may also be administered in the form of liposomes.

Applicants have demonstrated that VX-950 is orally bioavailable. Accordingly, preferred pharmaceutical compositions of this invention are formulated for oral administration.

For the CYP inhibitor, the dosage levels of between about 0.001 to about 200 mg/kg body weight per day, would be typical. More typical would be dosage levels of between about 0.1 to about 50 mg/kg or about 1.1 to about 25 mg/kg per day.

For preferred dosage forms of ritonavir, see U.S. Pat. No. 6,037,157, and the documents cited therein: U.S. Pat. No. 5,484,801, U.S. application Ser. No. 08/402,690, and International Applications WO 95/07696 and WO 95/09614).

Administrations in connection with this invention can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, the judgment of the treating physician and the severity of the particular disease being treated, prior treatment history, co-morbidities or concomitant medications, baseline viral load, race, duration of diseases, status of liver function and degree of liver fibrosis/cirrhosis, and the goal of therapy (eliminating circulating virus per-transplant or viral eradication). The amount of active ingredients will also depend upon the particular described compound and the presence or absence and the nature of the additional anti-viral agent in the composition.

According to another embodiment, the invention provides a method for treating a patient infected with a virus characterized by a virally encoded NS3/4A serine protease that is necessary for the life cycle of the virus by administering to said patient a pharmaceutically acceptable composition of this invention. Preferably, the methods of this invention are used to treat a patient suffering from a HCV infection. Such treatment may completely eradicate the viral infection or reduce the severity thereof. Preferably, the patient is a mammal. More preferably, the patient is a human being.

The dosages herein are preferably for use in vivo. Nevertheless, this is not intended as a limitation to using of these amounts of VX-950 for any purpose. In yet another embodiment the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

This invention also provides a process for preparing a composition comprising VX-950, or a pharmaceutically acceptable salt thereof, and a pharmaceutically acceptable carrier, adjuvant, or vehicle comprising the step of combining the VX-950, or the pharmaceutically acceptable salt thereof, and the pharmaceutically acceptable carrier, adjuvant, or vehicle, wherein the dosage of VX-950 in the composition is in accordance with any embodiment of this invention. An alternative embodiment of this invention provides a process wherein the composition comprises one or more additional agent as described herein.

This invention also provides a therapeutic regimens comprising VX-950, or a pharmaceutically acceptable salt thereof, at the dosages disclosed herein. In an alternative embodiment of this invention, the therapeutic regimen further comprises one or more of additional agent as described herein.

Pharmaceutical compositions may also be prescribed to the patient in "patient packs" containing the whole course of treatment in a single package, usually a blister pack. Patient packs have an advantage over traditional prescriptions, where a pharmacist divides a patients supply of a pharmaceutical from a bulk supply, in that the patient always has access to the package insert contained in the patient pack, normally missing in traditional prescriptions. The inclusion of a package insert has been shown to improve patient compliance with the physician's instructions.

It will be understood that the administration of the combination of the invention by means of a single patient pack, or patient packs of each formulation, containing within a package insert instructing the patient to the correct use of the invention is a desirable additional feature of this invention.

According to a further aspect of the invention is a pack comprising at least VX-950 (in dosages according to this invention) and an information insert containing directions on the use of the combination of the invention. Any composition, dosage form, therapeutic regimen or other embodiment of this invention may be presented in a pharmaceutical pack. In an alternative embodiment of this invention, the pharmaceutical pack further comprises one or more of additional agent as described herein. The additional agent or agents may be provided in the same pack or in separate packs.

Another aspect of this involves a packaged kit for a patient to use in the treatment of HCV infection or in the prevention of HCV infection (or for use in another method of this invention), comprising: a single or a plurality of pharmaceutical formulation of each pharmaceutical component; a container housing the pharmaceutical formulation(s) during storage and prior to administration; and instructions for carrying out drug administration in a manner effective to treat or prevent HCV infection.

Accordingly, this invention provides kits for the simultaneous or sequential administration of a dose of VX-950 (and optionally an additional agent). Typically, such a kit will comprise, e.g. a composition of each compound and optional additional agent(s) in a pharmaceutically acceptable carrier (and in one or in a plurality of pharmaceutical formulations) and written instructions for the simultaneous or sequential administration.

In another embodiment, a packaged kit is provided that contains one or more dosage forms for self administration; a container means, preferably sealed, for housing the dosage forms during storage and prior to use; and instructions for a patient to carry out drug administration. The instructions will typically be written instructions on a package insert, a label, and/or on other components of the kit, and the dosage form or forms are as described herein. Each dosage form may be individually housed, as in a sheet of a metal foil-plastic laminate with each dosage form isolated from the others in individual cells or bubbles, or the dosage forms may be housed in a single container, as in a plastic bottle. The present kits will also typically include means for packaging the individual kit components, i.e., the dosage forms, the container means, and the written instructions for use. Such packaging means may take the form of a cardboard or paper box, a plastic or foil pouch, etc.

A kit according to this invention could embody any aspect of this invention such as any composition, dosage form, therapeutic regimen, or pharmaceutical pack.

The packs and kits according to this invention optionally comprise a plurality of compositions or dosage forms. Accordingly, included within this invention would be packs and kits containing one composition or more than one composition.

Although certain exemplary embodiments are depicted and described below, it will be appreciated that compounds of this invention can be prepared according to the methods described generally above using appropriate starting materials generally available to one of ordinary skill in the art.

All cited documents are incorporated herein by reference.

In order that this invention be more fully understood, the following preparative and testing examples are set forth. These examples are for the purpose of illustration only and are not to be construed as limiting the scope of the invention in any way.

Example 1

HCV Replicon Cell Assay Protocol

Cells containing hepatitis C virus (HCV) replicon were maintained in DMEM containing 10% fetal bovine serum (FBS), 0.25 mg per ml of G418, with appropriate supplements (media A).

On day 1, replicon cell monolayer was treated with a trypsin:EDTA mixture, removed, and then media A was diluted into a final concentration of 100,000 cells per ml wit. 10,000 cells in 100 μl were plated into each well of a 96-well tissue culture plate, and cultured overnight in a tissue culture incubator at 37° C.

On day 2, compounds (in 100% DMSO) were serially diluted into DMEM containing 2% FBS, 0.5% DMSO, with appropriate supplements (media B). The final concentration of DMSO was maintained at 0.5% throughout the dilution series.

Media on the replicon cell monolayer was removed, and then media B containing various concentrations of compounds was added. Media B without any compound was added to other wells as no compound controls.

Cells were incubated with compound or 0.5% DMSO in media B for 48 hours in a tissue culture incubator at 37° C. At the end of the 48-hour incubation, the media was removed, and the replicon cell monolayer was washed once with PBS and stored at −80° C. prior to RNA extraction.

Culture plates with treated replicon cell monolayers were thawed, and a fixed amount of another RNA virus, such as Bovine Viral Diarrhea Virus (BVDV) was added to cells in each well. RNA extraction reagents (such as reagents from RNeasy kits) were added to the cells immediately to avoid degradation of RNA. Total RNA was extracted according to the instruction of manufacturer with modification to improve extraction efficiency and consistency. Finally, total cellular RNA, including HCV replicon RNA, was eluted and stored at −80° C. until further processing.

A Taqman real-time RT-PCR quantification assay was set up with two sets of specific primers and probe. One was for HCV and the other was for BVDV. Total RNA extractants from treated HCV replicon cells was added to the PCR reactions for quantification of both HCV and BVDV RNA in the same PCR well. Experimental failure was flagged and rejected based on the level of BVDV RNA in each well. The level of HCV RNA in each well was calculated according to a standard curve run in the same PCR plate. The percentage of inhibition or decrease of HCV RNA level due to compound treatment was calculated using the DMSO or no compound control as 0% of inhibition. The IC50 (concentration at which 50% inhibition of HCV RNA level is observed) was calculated from the titration curve of any given compound.

VX-950 demonstrated significant activity in the replicon assay. VX-950 was shown to have an $IC_{50}$ of 240 ng/ml and $IC_{90}$ of 476 ng/ml.

Example 2

HCV Ki Assay Protocol

HPLC Microbore Method for Separation of 5AB Substrate and Products
Substrate:
NH$_2$-Glu-Asp-Val-Val-(alpha)Abu-Cys-Ser-Met-Ser-Tyr-COOH A stock solution of 20 mM 5AB (or concentration of your choice) was made in DMSO w/0.2M DTT. This was stored in aliquots at −20 C.
Buffer: 50 mM HEPES, pH 7.8; 20% glycerol; 100 mM NaCl
Total assay volume was 100 μL

|  | X1 (μL) | conc. in assay |
| --- | --- | --- |
| Buffer | 86.5 | See above |
| 5 mM KK4A | 0.5 | 25 μM |
| 1 M DTT | 0.5 | 5 mM |
| DMSO or inhibitor | 2.5 | 2.5% v/v |
| 50 μM tNS3 | 0.05 | 25 nM |
| 250 μM 5AB (initiate) | 20 | 25 μM |

The buffer, KK4A, DTT, and tNS3 were combined; distributed 78 μL each into wells of 96 well plate. This was incubated at 30 C for ~5-10 min.

2.5 μL of appropriate concentration of test compound was dissolved in DMSO (DMSO only for control) and added to each well. This was incubated at room temperature for 15 min.

Initiated reaction by addition of 20 μL of 250 μM 5AB substrate (25 μM concentration is equivalent or slightly lower than the Km for 5AB).

Incubated for 20 min at 30 C.
Terminated reaction by addition of 25 μL of 10% TFA
Transferred 120 μL aliquots to HPLC vials
Separated SMSY product from substrate and KK4A by the following method:
Microbore Separation Method:
Instrumentation: Agilent 1100
Degasser G1322A
Binary pump G1312A
Autosampler G1313A
Column thermostated chamber G1316A
Diode array detector G1315A Column:
Phenomenex Jupiter; 5 micron C18; 300 angstroms; 150×2 mm; P/O 00F-4053-BO
Column thermostat: 40 C
Injection volume: 100 μL
Solvent A=HPLC grade water+0.1% TFA
Solvent B=HPLC grade acetonitrile+0.1% TFA

| Time (min) | % B | Flow (ml/min) | Max press. |
| --- | --- | --- | --- |
| 0 | 5 | 0.2 | 400 |
| 12 | 60 | 0.2 | 400 |
| 13 | 100 | 0.2 | 400 |
| 16 | 100 | 0.2 | 400 |
| 17 | 5 | 0.2 | 400 |

Stop time: 17 min
Post-run time: 10 min.

Example 3

VX-950 was examined in a randomized, double-blind, placebo-controlled single-dose escalation study. 25 healthy male volunteers were enrolled. Each subject received multiple single doses of VX-950 at least 7 days apart, 3 doses of VX-950 at increasing dose levels and 1 dose of placebo.

Doses of 25 mg to 1250 mg were evaluated. A dose escalation scheme was used that combined dose doubling and modified Fibonacci to be aggressive in the lower dose range and conservative in the higher dose range.

VX-950 was well tolerated at all dose levels and no serious adverse events were reported during the study. There did not appear to be an increase in adverse events with increasing dose levels.

Figure 1B:
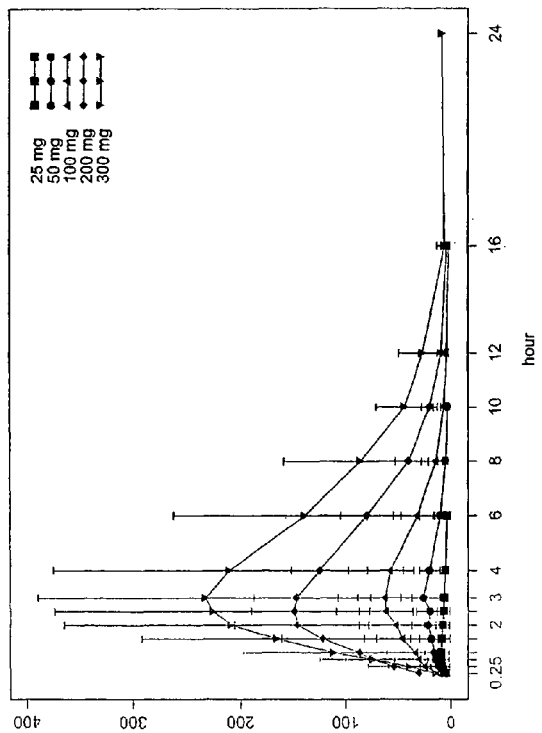

A pharmacokinetics analysis was performed using the statistical moment approach. FIG. 1A and FIG. 1B illustrate the mean concentration-time profiles. The selected derived pharmacokinetic parameters are depicted in FIGS. 2A-2D. Pharmacokinetic analysis showed that VX-950 was absorbed with a median $t_{max}$ of 3 hours. Less than 2% of VX-950 was eliminated unchanged in the urine, indicating that the drug is primarily eliminated via the metabolic route.

Example 4

Infectious Virus Assay

VX-950 demonstrated an $IC_{50}$ of 196 ng/ml in the infectious virus assy.

Example 5

VX-950 was examined in a randomized, placebo-controlled, multiple-dose, blinded, dose escalation study in 24 healthy subjects and 34 Hepatitis C positive subjects.

Healthy subjects were divided into 3 panels of 8 subjects each. In each panel, 6 subjects received VX-950 and 2 subjects received placebo. Healthy subjects were dosed with VX-950 at 450 mg, 750 mg, or 1250 mg q8h for 5 consecutive days. The healthy subjects were between the ages of 18-65 years (inclusive) and were Hepatitis B, Hepatitis C, and HIV negative. The males had a body mass index of 18.5-29.0 kg/m$^2$ (inclusive). The females had a body mass index of 18.5-32.5 kg/m$^2$ (inclusive).

Hepatitis C (genotype 1) positive subjects were divided into 3 panels of 12 subjects each. In each panel, 10 subjects received VX-950 and 2 subjects received placebo; in the 750 mg q8h group, 2 subjects withdrew prior to dosing so 8 subjects received the VX-950 and 2 received placebo. The HCV positive subjects were dosed with VX-950 at 450 mg or 750 mg, q8h or 1250 mg, q12h for 14 consecutive days.

VX-950 was well tolerated at all dose levels and no serious adverse events were reported during the study; mild and moderate adverse events were reported. All subjects completed the study.

Among the HCV positive subjects, the following percentages of subjects were treatment-naïve in the placebo, 450 mg q8h, 750 mg q8h, and 1250 mg q12h groups: 33.2%, 10%, 12.5%, and 30%, respectively.

The HCV positive subjects were tested post-treatment to monitor HCV RNA levels' return to baseline.

TABLE 1

Subject Baseline Characteristics

| | | VX-950 | | |
|---|---|---|---|---|
| | Placebo (n = 6) | 450 mg q8 h (n = 10) | 750 mg q8 h (n = 8) | 1250 mg q12 h (n = 10) |
| Sex, n (%) | | | | |
| Male | 3 (50.0) | 8 (80.0) | 3 (37.5) | 8 (80.0) |
| Female | 3 (50.0) | 2 (20.0) | 5 (62.5) | 2 (20.0) |
| Race, n (%) | | | | |
| Caucasian | 6 (100) | 10 (100) | 8 (100) | 10 (100) |
| Age, years | | | | |
| Median | 54.0 | 47.0 | 52.0 | 43.5 |
| Range | 31-64 | 33-64 | 46-64 | 25-62 |
| BMI, kg/m$^2$ | | | | |
| Median | 24.8 | 25.8 | 27.0 | 22.2 |
| Range | 21.0-29.0 | 22.6-28.4 | 21.1-29.4 | 21.2-24.3 |
| HCV RNA, log$_{10}$ IU/mL | | | | |
| Mean ± SD | 6.28 ± 0.47 | 6.54 ± 0.50 | 6.18 ± 0.47 | 6.46 ± 0.41 |
| Approximate years HCV infection, mean ± SD | 7.3 ± 7.6 | 9.2 ± 11.5 | 7.2 ± 7.6 | 6.9 ± 6.7 |
| HCV subtype, n (%) | | | | |
| 1* | 1 (16.7) | 0 | 2 (25.0) | 1 (10.0) |
| 1a | 2 (33.3) | 3 (30.0) | 1 (12.5) | 5 (50.0) |
| 1b | 3 (50.0) | 7 (70.0) | 5 (62.5) | 4 (40.0) |
| Prior hepatits C treatment, n (%) | 4 (66.7) | 9 (90.0) | 7 (87.5) | 7 (70.0) |

*Samples from 4 patients were classified as genotype 1 because the assay could not determine whether they were genotype 1a or 1b.
BMI, body mass index; HCV, hepatitis C virus; q8 h, every 8 hours; q12 h, every 12 hours; SD, standard deviation.
HCV RNA change from baseline, study VX04-950-101

TABLE 2

Maximum changes in HCV RNA by Category

| Change From Baseline in HCV RNA (log$_{10}$ IU/mL) | Placebo (n = 6) | VX-950 | | |
|---|---|---|---|---|
| | | 450 mg q8 h (n = 10) | 750 mg q8 h (n = 8) | 1250 mg q12 h (n = 10) |
| >−1 to <0 | 6 (100.0) | 0 | 0 | 0 |
| >−2 to ≦−1 | 0 | 0 | 0 | 0 |
| >−3 to ≦−2 | 0 | 1 (10.0) | 0 | 1 (10.0) |
| >−4 to ≦−3 | 0 | 7 (70.0) | 3 (37.5) | 9 (90.0) |
| >−5 to ≦−4 | 0 | 0 | 3 (37.5) | 0 |
| ≧−5 | 0 | 2 (20.0) | 2 (25.0) | 0 |

Values are n (%). q8 h, every 8 hours; q12 h, every 12 hours

Example 6

An oral dosage formulation was prepared as follows. VX-950 and povidone K29/32 were dissolved in methylene chloride, then sodium lauryl sulfate was added and dispersed in the solution to form a homogenous suspension. This suspension was spray-dried using an inlet temperature of 90° C. and an outlet temperature of 56° C., and the product was collected from the cyclone. The spray-dried dispersion was fluid-bed dried at 75° C. for 8 hours. The resultant powder was pre-measured into glass vials, and just prior to dosing was suspended in water (30 mL) for administration to the subjects. In connection with dosing, each vial was washed with 3 separate portions of water, with the total volume of water being 90 mL.

| VX-950 Solid Dispersion | | |
|---|---|---|
| % (w/w) | Ingredient | |
| 49.5 | VX-950 | Spray-dried from CH$_2$Cl$_2$ |
| 49.5 | PVP K29/32 | |
| 1 | SLS | |

Example 7

Detection of HCV RNA was done using the Roche COBAS TaqMan HCV/HPS assay, available from Roche molecular Diagnostics. Other assays are available.

Example 8

Serum neopterin concentrations were measured by a quantitative competitive ELISA (ELItest® Neopterin, Brahms, Hennigsdorf, Germany) at pretreatment, at day 7 and 14, and at day 7-10 of follow-up. The lower limit of detection (LLD) was 2 nmol/l.

Example 9

Serum ALT was measured using commercially available methods.

Example 10

VX-950 Validation in Human Plasma

VX-950

Stock solution: 0.961 mg/ml of VX-950 in 2-propanol (10.0 ml)

Diluted stock solution 1: 96.1 μg/ml of VX-950 in 2-propanol (5.00 ml)

Diluted stock solution 2: 9.61 μg/ml of VX-950 in 2-propanol (10.0 ml)

Diluted stock solution 3: 0.961 μg/ml of VX-950 in 2-propanol (10.0 ml)

The stock and diluted stock solutions were stored in capped borosilicate tubes (11.5 ml) at −20° C.

9.1.3 Internal Standard (Compound 1)

Stock solution: 1.00 mg/ml of Compound 1 (a close structural analog of VX-950) in 2-propanol (5.00 ml)

Working solution: 300 ng/ml of Compound 1 in acetonitrile (100 ml)

The stock solution was stored in a capped borosilicate tube (11.5 ml); the working solution in a capped borosilicate bottle (100 ml), all at −20° C.

Sample Preparation

Aliquots of 100 μl of plasma, 100 μl of internal standard working solution (or acetonitrile for blank samples) was added to an extraction tube. After vortex mixing for 30 seconds, 500 μl of toluene was added and extraction was performed by vortex mixing for 30 seconds. After centrifugation at 3000 rpm at +4° C. for 5 minutes, the aqueous layer was frozen in a mixture of acetone and dry ice and the organic layer transferred to another extraction tube. 50 μl of 2,2-dimethoxypropane was added and the samples were evaporated to dryness under nitrogen at approximately +30° C. The residue was redissolved in 300 μl of heptane:acetone (90:10, v/v) [or heptane:THF (80:20, v/v)] by vortex mixing for 60 seconds. The sample was transferred to an injection vial and an aliquot of 60 μl was injected into the chromatographic system.

Chromatographic Conditions

Mobile phase: (Isocratic elution) heptane:acetone methanol (80:19:1, v/v/v)

Make-up Solvent: acetonitrile:acetone:methanol formic acid (40:60:1:1, v/v/v/v)

Column temperature: −1° C.

Flow rate: 1.00 ml/min (of which: 0.750 ml/min mobile phase and 0.250 ml/min make-up solvent) (completely transferred to detector)

Injection volume: 60 μl

Autosampler temperature: +3° C.

ADDITIONAL REFERENCES

Wasley A, Alter M J. Epidemiology of hepatitis C: geographic differences and temporal trends. Semin Liver Dis 2000; 20:1-16.

Alter H J, Seeff L B. Recovery, persistence, and sequelae in hepatitis C virus infection: a perspective on long-term outcome. Semin Liver Dis 2000; 20:17-35.

Brown R S Jr, Gaglio P J. Scope of worldwide hepatitis C problem. Liver Transpl 2003; 9:S10-S13.

DeFrancesco R, Migliaccio G. Challenges and successes in developing new therapies for hepatitis C. Nature 2005; 436(7053):953-60.

Bowen D G, Walker C M. The origin of quasispecies: cause or consequence of chronic hepatitis C viral infection? J Hepatol 2005; 42:408-17.

Hoofnagle J H. Course and outcome of hepatitis C. Hepatology 2002; 36:S21-S29.

Brown R S Jr. Hepatitis C and liver transplantation. Nature 2005; 436(7053):973-8.

Chisari F V. Unscrambling hepatitis C virus-host interactions. Nature 2005; 436(7053):930-2.

All of the documents cited herein, are incorporated herein by reference.

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments that have been represented by way of example above.

We claim:

1. A therapeutic regimen comprising administering for a period of at least 14 days:
   a. VX-950, or a pharmaceutically acceptable salt thereof, three times per day in an amount of about 750 mg;
   b. pegylated interferon in an amount of about 180 μg/wk; and
   c. ribavirin.

2. The regimen of claim 1, wherein the amount of VX-950 is administered every 8 hours.

* * * * *

UNITED STATES PATENT AND TRADEMARK OFFICE
CERTIFICATE OF CORRECTION

| | | |
|---|---|---|
| PATENT NO. | : 8,431,615 B2 | Page 1 of 1 |
| APPLICATION NO. | : 11/264746 | |
| DATED | : April 30, 2013 | |
| INVENTOR(S) | : Chu et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1077 days.

Signed and Sealed this
Eleventh Day of November, 2014

Michelle K. Lee
*Deputy Director of the United States Patent and Trademark Office*